US007881873B2

(12) United States Patent
Akilesh et al.

(10) Patent No.: US 7,881,873 B2
(45) Date of Patent: Feb. 1, 2011

(54) SYSTEMS AND METHODS FOR STATISTICAL GENOMIC DNA BASED ANALYSIS AND EVALUATION

(75) Inventors: Shreeram Akilesh, Bangor, ME (US); Kevin D. Mills, Bar Harbor, ME (US); Derry Charles Roopenian, Salisbury Cove, ME (US); Daniel J. Shaffer, Bar Harbor, ME (US)

(73) Assignee: The Jackson Laboratory, Bar Harbor, ME (US)

( * ) Notice: Subject to any disclaimer, the term of this patent is extended or adjusted under 35 U.S.C. 154(b) by 1345 days.

(21) Appl. No.: 11/341,699

(22) Filed: Jan. 27, 2006

(65) Prior Publication Data

US 2006/0129331 A1 Jun. 15, 2006

Related U.S. Application Data

(63) Continuation-in-part of application No. 10/835,541, filed on Apr. 29, 2004, now abandoned.

(60) Provisional application No. 60/466,362, filed on Apr. 29, 2003.

(51) Int. Cl.
*G01N 33/48* (2006.01)
(52) U.S. Cl. ..................................................... 702/19
(58) Field of Classification Search ....................... None
See application file for complete search history.

(56) References Cited

U.S. PATENT DOCUMENTS

| 6,180,349 | B1 | 1/2001 | Ginzinger et al. |
| 6,263,287 | B1 | 7/2001 | Zheng et al. |
| 2002/0103604 | A1 | 8/2002 | Liu et al. |

FOREIGN PATENT DOCUMENTS

| EP | 1 037 158 A2 | 9/2000 |
| EP | 1 138 783 A2 | 4/2001 |
| WO | WO 99/54510 | 10/1999 |
| WO | WO 02/08461 A2 | 1/2002 |
| WO | WO 02/08461 A2 | 1/2002 |
| WO | WO 02/08461 A3 | 1/2002 |

OTHER PUBLICATIONS

Ginzinger et al. (Cancer Research vol. 60, p. 5405-5409, 2000).*
Bilban et al. (Current issues in Mol. Biol., vol. 4, p. 57-64, 2002).*
Zhang, et al. (Birth Defects Research: Part A, vol. 67, p. 533-544, 2003).
Zien et al. (Bioinformatics, vol. 17, Suppl. 1, S323-S331, 2001).
Akilesh, S., "Global Pattern Recognition, A Software Algorithm for Gene Expression Analysis," Genome Research, 13(7):1719-1727 (2003).
Akilesh, S., et al., "Customized Molecular Phenotyping by Quantitative Gene Expression and Pattern Recognition Analysis," Genome Research, 13:1719-1727 (2003).
International Search Report from PCT/US2007/002167, dated Mar. 11, 2008.
Ginzinger, D.G., "Gene quantification using real-time quantitative PCR: An emerging technology hits the mainstream," Experimental Hematology, 30:503-512 (2002).
Suzuki, S., et al., "Comparative Study between DNA Copy Number Aberrations Determined by Quantitative Microsatellite Analysis and Clinical Outcome in Patients with Stomach Cancer," Clinical Cancer Research, 10:3013-3019 (2004).
Jo Vandesompele, et al., Accurate Normalization of real-time quantitative RT-PCR data by geometric averaging of multiple internal control genes. Genome Biology 3(7) 1-12, 2002.
Claverie, J. et al., "Computational Methods for the Identification of Differential and Coordinated Gene Expression," Human Molecular Genetics, 8(10):1821-1832 (1999).
Hamalainen, H. K. et al., "Identification and Validation of Endogenous Reference Genes for Expression Profiling of T Helper Cell Differentiation by Quantitative Real-Time RT-PCR," Analytical Biochemistry, 299:63-70 (2001).
Tseng, G. C. et al., "Issues in cDNA Microarray Analysis: Quality Filtering, Channel Normalization, Models of Variations and Assessment of Gene Effects," Nucleic Acids Research 29(12):2549-2557.
Bilban et al., "Normalizing DNA Microarray Data," Current ssues in Mol. Biol. 4:57-64 (2002).

\* cited by examiner

*Primary Examiner*—Karlheinz R Skowronek
(74) *Attorney, Agent, or Firm*—McDermott Will & Emery LLP

(57) ABSTRACT

Systems and methods for performing rapid genomic DNA analysis of samples, such as control samples and experimental samples. In one aspect, the system makes use of genomic DNA input, rather than gene expression input such as mRNA and/or cDNA associated with mRNA. The systems and methods perform statistical analyses on data generated from the samples to determine which DNA sequences in an identified set of DNA sequences have a basis of variation in an experimental sample when compared to a control sample, and additionally provide a quantitative measure of this variation. The quantitative measure may be based on metrics such as copy number and/or fold-change. The systems and methods employ this statistical framework in DNA-based evaluation settings, including the evaluation/diagnosis of a pathological condition such as cancer or transgenic analysis of transgenic plants and animals. The systems and methods also provide means to select and refine the selection of DNA sequences, such as genes, known to undergo copy change for a particular pathological condition. This leads to the creation of stock gene sets catered to individual application areas and/or clinical uses, which may be used with the systems and methods described in this application for the purpose of, for example, a clinical kit for rapid DNA-based evaluation.

46 Claims, 11 Drawing Sheets

Figure 2

| Gene | Normalizer | | | |
|---|---|---|---|---|
| | A | B | C | D |
| A | * | A-B | A-C | A-D |
| B | B-A | * | B-C | B-D |
| C | C-A | C-B | * | C-D |
| D | D-A | D-B | D-C | * |

Figure 4

Normalizer

| Gene | A | B | C | D | | # hits |
|------|---|---|---|---|---|--------|
| A | * | not | sig | not | → | 1 |
| B | sig | * | sig | sig | → | 3 |
| C | not | not | * | sig | → | 1 |
| D | sig | not | sig | * | → | 2 |

Figure 6

| alpha= | 0.05 | Cycle cutoff= | 37.5 | | |
|---|---|---|---|---|---|
| | | 270 | 275 | | |
| | | Group 1 | | Group 2 | |
| # | Gene # | Gene Name | | | |
| 1 | A01 | IgM | 27.600538 | 28.003075 | 28.061571 | 28.511885 | 28.247877 | 27.977549 |
| 2 | A02 | Hoxd11 | 28.181684 | 28.20333 | 28.283792 | 28.681824 | 28.713282 | 28.525028 |
| 3 | A03 | IgG3 | 27.498066 | 27.445223 | 27.567112 | 28.48302 | 26.297491 | 26.855328 |
| 4 | A04 | Hoxd10 | 23.876808 | 23.76587 | 23.69896 | 24.207165 | 24.05467 | 24.162254 |
| 5 | A05 | IgG2c | 30.912794 | 31.404142 | 29.953072 | 28.09847 | 27.357 | 28.503567 |
| 6 | A06 | Hoxd1 | 26.622854 | 26.106195 | 26.049122 | 27.460516 | 27.39698 | 27.508114 |
| 7 | A07 | IgG2bs | 32.071186 | 33.20178 | 31.016777 | 29.146482 | 28.484875 | 28.63583 |
| 8 | A08 | Hoxc13 | 26.114983 | 25.855755 | 25.704844 | 26.295954 | 26.108757 | 26.049673 |
| 9 | A09 | IgG2bm | 28.475851 | 28.308231 | 26.82357 | 27.296876 | 27.243574 | 27.507206 |
| 10 | A10 | Hoxa9 | 30.233234 | 30.90268 | 29.762488 | 30.879175 | 30.771854 | 30.599798 |
| 11 | A11 | IgG2a | 31.971455 | 30.583199 | 31.65727 | 27.318434 | 27.066638 | 27.299957 |
| 12 | A12 | Hoxa7 | 30.377314 | 30.833145 | 30.333136 | 31.648157 | 31.307898 | 31.230764 |
| 13 | A13 | IgG1s | 30.54601 | 30.19681 | 30.32347 | 26.405722 | 26.35037 | 26.627905 |
| 14 | A14 | Hoxa4 | 27.06318 | 26.683315 | 26.241991 | 26.93433 | 27.300077 | 26.95405 |
| 15 | A15 | IgG1m | 29.705835 | 30.050186 | 30.305918 | 27.032696 | 27.218004 | 27.36302 |
| 16 | A16 | Hoxa13 | 30.546362 | 30.365648 | 30.204412 | 31.29787 | 31.032156 | 30.700169 |
| 17 | A17 | IgE | 29.07946 | 29.317379 | 29.364916 | 27.926971 | 28.349455 | 28.462767 |
| 18 | A18 | Hoxa11 | 33.662773 | 34.918385 | 33.427892 | 37.574883 | 36.918907 | 34.047394 |
| 19 | A19 | IgA | 28.861639 | 29.17911 | 28.39674 | 28.908373 | 28.970215 | 28.737158 |
| 20 | A20 | Hoxa1 | 29.684284 | 28.988873 | 29.01099 | 29.371134 | 29.78127 | 29.401665 |
| 21 | A21 | Ly6a | 31.270805 | 30.427351 | 30.614239 | 30.498983 | 30.731892 | 30.607087 |
| 22 | A22 | Hlxb9 | 27.93387 | 27.906443 | 27.519482 | 27.898977 | 28.117674 | 28.178917 |
| 23 | A23 | Il21r | 30.01379 | 29.998613 | 29.654716 | 30.293264 | 29.797174 | 29.628006 |
| 24 | A24 | Wnt5b | 32.9918 | 34.997456 | 32.0274 | 34.022038 | 34.225204 | 33.433125 |
| 25 | B01 | Wt1 | 31.837093 | 31.561472 | 31.688938 | 31.611168 | 32.864803 | 30.789425 |
| 26 | B02 | Zfpn1a3 | 24.993334 | 24.771729 | 24.641485 | 25.54012 | 25.547543 | 25.502052 |
| 27 | B03 | Tsg101 | 32.3637 | 32.550438 | 32.91622 | 40 | 40 | 40 |
| 28 | B04 | Zfpn1a2 | 28.084711 | 27.879927 | 27.454325 | 27.898977 | 29.053963 | 40 |
| 29 | B05 | Trp53 | 27.73869 | 27.367843 | 27.254604 | 40 | 30.923153 | 40 |
| 30 | B06 | Zfhx1b | 35.289566 | 39.36927 | 34.946395 | 40 | 40 | 40 |
| 31 | B07 | Tgfb1 | 36.038383 | 33.80667 | 33.249447 | 40 | 40 | 40 |
| 32 | B08 | Yy1 | 30.876333 | 29.920061 | 30.893318 | 34.049755 | 31.3658 | 32.799995 |

Figure 8a

| # | Gene # | Gene Name | t-test | Is number? | Healthy | Sick | Data Gene? | Qualifier? |
|---|--------|-----------|--------|------------|---------|------|------------|------------|
| 1 | A01 | IgM | 0.167 | TRUE | 1 1 1 | 1 1 1 | TRUE | TRUE |
| 2 | A02 | Hoxd11 | 0.009 | TRUE | 1 1 1 | 1 1 1 | TRUE | TRUE |
| 3 | A03 | IgG3 | 0.024 | TRUE | 1 1 1 | 1 1 1 | TRUE | TRUE |
| 4 | A04 | Hoxd10 | 0.007 | TRUE | 1 1 1 | 1 1 1 | TRUE | TRUE |
| 5 | A05 | IgG2c | 0.008 | TRUE | 1 1 1 | 1 1 1 | TRUE | TRUE |
| 6 | A06 | Hoxd1 | 0.020 | TRUE | 1 1 1 | 1 1 1 | TRUE | TRUE |
| 7 | A07 | IgG2bs | 0.025 | TRUE | 1 1 1 | 1 1 1 | TRUE | TRUE |
| 8 | A08 | Hoxc13 | 0.153 | TRUE | 1 1 1 | 1 1 1 | TRUE | TRUE |
| 9 | A09 | IgG2bm | 0.427 | TRUE | 1 1 1 | 1 1 1 | TRUE | TRUE |
| 10 | A10 | Hoxa9 | 0.304 | TRUE | 1 1 1 | 1 1 1 | TRUE | TRUE |
| 11 | A11 | IgG2a | 0.009 | TRUE | 1 1 1 | 1 1 1 | TRUE | TRUE |
| 12 | A12 | Hoxa7 | 0.014 | TRUE | 1 1 1 | 1 1 1 | TRUE | TRUE |
| 13 | A13 | IgG1s | 0.000 | TRUE | 1 1 1 | 1 1 1 | TRUE | TRUE |
| 14 | A14 | Hoxa4 | 0.231 | TRUE | 1 1 1 | 1 1 1 | TRUE | TRUE |
| 15 | A15 | IgG1m | 0.001 | TRUE | 1 1 1 | 1 1 1 | TRUE | TRUE |
| 16 | A16 | Hoxa13 | 0.045 | TRUE | 1 1 1 | 1 1 1 | TRUE | TRUE |
| 17 | A17 | IgE | 0.011 | TRUE | 1 1 1 | 1 1 1 | TRUE | TRUE |
| 18 | A18 | Hoxa11 | 0.172 | TRUE | 1 1 1 | 0 1 1 | TRUE | FALSE |
| 19 | A19 | IgA | 0.823 | TRUE | 1 1 1 | 1 1 1 | TRUE | TRUE |
| 20 | A20 | Hoxa1 | 0.347 | TRUE | 1 1 1 | 1 1 1 | TRUE | TRUE |
| 21 | A21 | Ly6a | 0.604 | TRUE | 1 1 1 | 1 1 1 | TRUE | TRUE |
| 22 | A22 | Hlxb9 | 0.166 | TRUE | 1 1 1 | 1 1 1 | TRUE | TRUE |
| 23 | A23 | Il21r | 0.945 | TRUE | 1 1 1 | 1 1 1 | TRUE | TRUE |
| 24 | A24 | Wnt5b | 0.596 | TRUE | 1 1 1 | 1 1 1 | TRUE | TRUE |
| 25 | B01 | Wt1 | 0.931 | TRUE | 1 1 1 | 1 1 1 | TRUE | TRUE |
| 26 | B02 | Zfpn1a3 | 0.018 | TRUE | 1 1 1 | 1 1 1 | TRUE | TRUE |
| 27 | B03 | Tsg101 | 0.000 | TRUE | 1 1 1 | 1 1 1 | TRUE | FALSE |
| 28 | B04 | Zfpn1a2 | 0.144 | TRUE | 1 1 1 | 0 0 0 | TRUE | FALSE |
| 29 | B05 | Trp53 | 0.088 | TRUE | 1 1 1 | 0 1 0 | FALSE | FALSE |
| 30 | B06 | Zfhx1b | 0.136 | TRUE | 1 0 1 | 0 0 0 | TRUE | FALSE |
| 31 | B07 | Tgfb1 | 0.022 | TRUE | 1 1 1 | 1 1 1 | TRUE | TRUE |
| 32 | B08 | Yy1 | 0.091 | TRUE | 1 1 1 | 1 1 1 | TRUE | TRUE |
| 33 | B09 | Rel | 0.003 | TRUE | 1 1 1 | 1 1 1 | TRUE | TRUE |
| 34 | B10 | Tcf1 | 0.093 | TRUE | 1 1 1 | 1 1 1 | TRUE | TRUE |

Figure 8b

| alpha | 0.05 | Cycle cutoff | 37.5 | *Fold Change with respect to | |
|---|---|---|---|---|---|
| Data Genes | 381 | Qualifiers | 372 | | |
| Position | Gene | # Total hits | Score | 10 best normalizers | Rank |
| B03 | Tsg101 | 370 | 0.995 | -151.67 | 1 |
| B07 | Tgfb1 | 368 | 0.989 | -54.08 | 2 |
| A13 | IgG1s | 363 | 0.976 | 17.03 | 3 |
| A11 | IgG2a | 360 | 0.968 | 19.61 | 4 |
| A15 | IgG1m | 353 | 0.949 | 7.77 | 5 |
| B23 | Nmyc1 | 352 | 0.946 | 7.04 | 6 |
| A05 | IgG2c | 349 | 0.938 | 7.80 | 7 |
| A07 | IgG2bs | 338 | 0.909 | 10.18 | 8 |
| F09 | Fgr | 311 | 0.836 | -3.23 | 9 |
| G06 | Notch1 | 304 | 0.817 | 3.32 | 10 |
| P23 | Suv39h1 | 248 | 0.667 | 2.25 | 11 |
| P20 | Ptch2 | 245 | 0.659 | -3.98 | 12 |
| A03 | IgG3 | 244 | 0.656 | 2.24 | 13 |
| A17 | IgE | 237 | 0.637 | 2.30 | 14 |
| A06 | Hoxd1 | 233 | 0.626 | -2.01 | 15 |
| C12 | Wnt1 | 221 | 0.594 | -2.86 | 16 |
| G05 | Tnf | 186 | 0.500 | 1.98 | 17 |
| G16 | Jag1 | 173 | 0.465 | -1.70 | 18 |
| L15 | Malt1 | 168 | 0.452 | -2.06 | 19 |
| M19 | Cxcl12 | 164 | 0.441 | -2.14 | 20 |
| D05 | Myc | 162 | 0.435 | -1.93 | 21 |
| K09 | Fcgr2b | 154 | 0.414 | 1.62 | 22 |
| N09 | Biklk | 141 | 0.379 | -1.58 | 23 |
| G04 | Bmi1 | 136 | 0.366 | 1.36 | 24 |
| H05 | Cdkn1b | 135 | 0.363 | -1.66 | 25 |
| B02 | Zfpn1a3 | 134 | 0.360 | -1.45 | 26 |
| M10 | Fzd6 | 133 | 0.358 | 1.56 | 27 |
| C09 | Il4ra | 127 | 0.341 | -1.44 | 28 |
| B09 | Rel | 118 | 0.317 | -1.40 | 29 |
| K01 | Cd19 | 118 | 0.317 | 1.83 | 30 |
| P24 | Nfkbib | 116 | 0.312 | -1.56 | 31 |
| L18 | Igf1r | 115 | 0.309 | -1.45 | 32 |

Figure 9

SYSTEMS AND METHODS FOR STATISTICAL GENOMIC DNA BASED ANALYSIS AND EVALUATION

RELATED APPLICATIONS

This application claims the benefit of and is a continuation in part of U.S. patent application Ser. No. 10/835,541, filed on Apr. 29, 2004, which claims the benefit of U.S. provisional application 60/466,362, filed on Apr. 29, 2003, the contents of which are incorporated by reference herein in their entirety.

REFERENCE TO GOVERNMENT CONTRACTS

This invention was made with Government support awarded by the National Institutes of Health under Contract Nos. RO-1-DK-56597, RO-1-HL-65749, RO-1-AI-28802, and P30-CA-034196. The Government has certain rights in this invention.

BACKGROUND

Existing methods for DNA-based profiling have drawbacks which compromise their accuracy, efficiency, ease of use, and scalability. For example, DNA profiling methods such as karyotyping and fluorescent in situ hybridization (FISH) are time consuming and technically demanding. DNA microarray hybridization technologies, such as comparative genome hybridization (CGH) and Representational Oligonucleotide Microarray Analysis (ROMA), are similarly time consuming, require large amounts of input DNA material, and a considerable expenditure in specialized equipment. These and other drawbacks prevent the widespread adoption of genetic profiling methods for clinical use.

Real-time quantitative, polymerase chain reaction techniques (QPCR) are accepted as a gold standard for quantitative analysis of DNA. However, such techniques have generally only been applied to analyze a small number of target DNA sequences because of the lack of an analytical algorithm with sufficient statistical power to provide reliable data for a robust set of target DNA sequences of interest.

Thus, a need exists for efficient, easy to use, rapid, accurate, and scalable systems and methods for DNA-based profiling that can be used in, for example, clinical use for diagnosis and/or evaluation. It is desirable that the systems and methods supplant less sensitive, hybridization based methodologies and provide the high sensitivity achieved with QPCR methods. It is also desirable that the systems and methods overcome the analytical limitations encumbered by conventional computational methods typically confounding QPCR analyses. It is also desirable that the systems and methods be customizable to a diverse set of applications or customizable for individual patients. It is also desirable that the systems and methods only require readily attainable and small amounts of input samples. Finally, it is desirable that the systems and methods are capable of identifying, for each application area of interest, the appropriate target DNA sequences that are most relevant for DNA-based analysis for that application.

SUMMARY

Disclosed herein are systems and methods for performing rapid genomic DNA analysis of samples, such as control samples and experimental samples, and uses for such DNA-based diagnosis and/or evaluation. Rapid genomic DNA analysis includes the observation, handling, processing, and analysis of genomic DNA, data associated with genomic DNA, and systems and methods that employ genomic DNA as an input. Genomic DNA generally refers to DNA from the genome of an organism, such as, but not limited to, a mammal or other higher-order species. A benefit of the systems and methods described herein is their use of genomic DNA input, rather than gene expression input such as mRNA and/or cDNA associated with mRNA, as will be discussed herein. The statistical techniques employed for analyzing the genomic DNA data may be referred to as Global Pattern Recognition (GPR)-based techniques.

The systems and methods can be used to perform statistical analyses on data generated from samples to determine which DNA sequences in an identified set of DNA sequences have a basis of variation in an experimental sample when compared to a control sample, and additionally provide a quantitative measure of this variation. The quantitative measure may be based on metrics such as copy number and/or fold-change. The systems and methods employ this statistical framework in DNA-based evaluation/diagnosis settings, including the evaluation of a pathological condition such as cancer or transgenic analysis of transgenic plants and animals. The systems and methods also provide means to select and refine the selection of DNA sequences, such as genes, known to undergo copy change for a particular pathological condition. This leads to the creation of stock gene sets catered to individual application areas and/or clinical uses, which may be used with the systems and methods described in this application for the purpose of, for example, a clinical kit for rapid DNA-based diagnosis.

The methods include furnishing the samples using microtiter, microarray plates, and/or other suitable mechanisms. In embodiments discussed herein, the samples are provided on an array, which may include a device allowing for measurement and/or visualization of differential expression and/or amplification activity. The method performs a statistical analysis on a set of target DNA sequences (i.e., DNA sequences of interest) within the samples using genomic DNA as its input. DNA amplification and/or detection is performed on the samples. The DNA amplification/detection methods used in various embodiments may include PCR-based methods (i.e. QPCR), isothermal amplification methods (i.e. rolling circle amplification), and/or signal amplification/detection techniques known in the art. Isothermal methods refer to methods that are performed with little or substantially no temperature change. The statistical analysis includes automated methods for determining a set of qualifier DNA sequences which will serve as a baseline for comparison when analyzing the DNA sequences of interest. For each DNA sequence of interest and qualifier DNA sequence pair, a numerical measure (cycle threshold value) related to the copy number level is determined for both the DNA sequence of interest and the qualifier DNA sequence. These cycle threshold values are compared, and this is done for all or substantially all samples. The results for the control samples are compared to the results for the experimental samples to determine whether a statistically significant change occurred. This is done, in one practice, using a hypothesis test, such as, for example, a T-test. By aggregating and processing data thus collected for each DNA sequence of interest with respect to each identified qualifier, the methods provide a ranked list of the DNA sequences of interest whose copy numbers have varied in the experimental sample when compared to the control sample. The ranked list is then processed to determine quantitative measures of the copy number changes, such as the fold changes of the DNA sequences. As will be described herein, the fold changes are related to a multiple of increase or decrease of a particular DNA sequence in the experimental samples compared to the control samples, and are computed with respect to one or more normalizer DNA sequences, which the method itself identifies. The selection of a DNA sequence to be a normalizer DNA sequence is typically dependent on the reproducibility of its detection across the samples. DNA sequences with reproducibility of detection across samples generally refers to DNA sequences that have similar copy number levels across the samples, and for which detection methods associated with the copy number levels (such as cycle threshold (CT) evaluation) yield similar results. These quantitative measures can be mapped into a diagnosis or evaluation, such as a diagnosis/prognosis of a pathological condition (i.e., cancer), or an evaluation of a transgenic plant or animal.

In another aspect, the systems and methods can be used to determine which DNA sequences should be included as target DNA sequences when conducting genomic DNA analysis for a particular application. The systems and methods can be used to identify sets of DNA sequences that have a basis for variation in a phenomenon of interest such as a particular pathological condition. In addition to developing DNA sequence sets specific to a pathological condition, the systems and methods can identify DNA sequence sets specific to a particular patient, or to a particular stage of a pathological condition. This leads to the development of DNA sequence sets catered to individual application areas. The DNA sequence sets can be used within a kit for rapid DNA-based evaluation and/or diagnosis. The kit may be suitable for clinical use. Part of the appeal and utility of the systems and methods is that rather than studying a particular DNA sequence in a variety of situations, they can be used to understand the profile of a large array of DNA sequences under various conditions. By identifying both qualitative trends/patterns among the set of DNA sequences as a whole and also quantitative measures of the changes of specific DNA sequences, the systems and methods provide a useful system to gain both general insights and practical information towards understanding which DNA sequence variations are correlated with particular pathological conditions.

In one embodiment, the methods are realized as software processes. For example, the methods may be realized as Microsoft Excel-based software programs that output a ranked list of statistically changed DNA sequences using raw input data (such as cycle threshold "CT" values) from 48 to 384 target DNA sequences in up to five control replicates and five experimental replicates. The input data can be collected by making use of, for example, a 384-well array. The method compares the datasets from both groups using Excel's Students T-test after a multiple DNA sequence normalization. The invention thus enables a recognition of a change in DNA sequence copy number. In one aspect, the invention uses the power of biological replicates and the sensitivity of realtime PCR techniques to extract the most statistically changed DNA sequences, even if the fold change is small.

In one aspect, the statistical processing steps, including the identification of and normalization against multiple qualifier DNA sequences, provide for more accurate identification of DNA sequence copy number variation within a framework that is scalable to efficiently and rapidly handle large data sets. In another aspect, there are provided methods to proceed from DNA input, to an identification of DNA sequences with significant copy number changes, to a determination of a quantitative measure of the copy number changes, to an evaluation and/or diagnosis of a pathological condition. The use of genomic DNA input as opposed to, for example, mRNA/cDNA input, is advantageous for allowing easier access to and processing of input samples, and provides different information than gene expression data. The method may require smaller sample sizes than other methods known in the art, and may be employed with as little as one biopsy specimen. Furthermore, the systems and methods can make use of control samples collected from a patient using simple and non-invasive techniques such as a cheek swab/scrape. The systems also allow for easier collection of experimental samples from, for example, a cancer tumor, and therefore provides for efficient clinical use. Additionally, using the present invention to identify DNA sequence sets of interest customized to particular applications further enhances the accuracy of subsequent evaluation or diagnosis attempts for that application. The above features and others make the present invention particularly well suited for clinical evaluative and diagnostic kits.

As contemplated by this application, an "array" may include any array depicting properties of a subject, for example, a gene or protein microarray or macroarry.

The systems and methods relate to the analysis of DNA sequences. In some embodiments, the DNA sequences are genes, in others the DNA sequences are within genes, and in others still the DNA sequences are not within genes. It is to be understood in this application that certain embodiments may be discussed in the context of genes by may be equally applicable for the case of DNA sequences in general.

In another aspect, this invention relates to a method for rapid genomic DNA analysis on samples, comprising furnishing an array having a plurality of primers for detecting target DNA sequences, performing a genomic DNA detection process with the array to collect a reaction product dataset which includes data associated with the target DNA sequences, identifying a subset of the target DNA sequences to be used in comparison and normalization of the target DNA sequences, performing a statistical analysis of the reaction product data set by comparing data associated with the target DNA sequences to data associated with the identified subset of target DNA sequences, and determining a relative abundance of one or more of the target DNA sequences in at least one of the samples.

The DNA detection process can include at least one of a DNA amplification process, a DNA signal detection process, and a DNA signal amplification process.

Performing a statistical analysis of the reaction product data set can include determining a statistically ranked list of a plurality of the target DNA sequences based on respective statistical variations of the data associated with the plurality of the target DNA sequences between control samples and experimental samples.

Furnishing an array can include providing a plurality of arrays having a plurality of control samples and a plurality of experimental samples.

The samples can include a plurality of control sample replicates and a plurality of experimental sample replicates. The samples include at least 3 control sample replicates and at least 3 experimental sample replicates. Each of the control sample replicates can be taken from a same sample. Each of the experimental sample replicates can be taken from a same sample.

The target DNA sequences can include DNA sequences that are one of genes, within genes, and not within genes. The target DNA sequences can include transgenes of at least one of a transgenic plant and a transgenic animal. Performing a DNA detection process can include performing Real Time PCR, performing an isothermal DNA amplification process such as one of rolling circle amplification, Invader assay, or helicase-dependent amplification.

The methods of the invention may include determining a cycle cut-off parameter representative of a maximum number of cycles to perform and limiting cycles according to the cycle cut-off parameter. They may also include measuring parameters representative of a cycle threshold for respective target DNA sequences.

The methods may include determining a set of non-informative DNA sequences among the target DNA sequences, and discarding data associated with the set of non-informative DNA sequences from the reaction product data set.

The step of determining a set of non-informative DNA sequences may include detecting a DNA sequence having a cycle threshold greater than a cut-off cycle in a control sample and an experimental sample.

Identifying a subset of target DNA sequences may include analyzing the reaction product dataset to identify DNA sequences for inclusion in the subset based on their amplification activity. Identifying a subset of target DNA sequences may include identifying a DNA sequence having a cycle threshold greater than a cut-off cycle for any one of the samples and excluding the DNA sequence from the subset.

Performing a statistical analysis of the reaction product dataset may include, for a target DNA sequence, determining differences in cycle threshold values between the target DNA sequence and respective DNA sequences in the identified subset.

Performing a statistical analysis of the DNA sequences may include, for a target DNA sequence, determining differences in cycle threshold values for the target DNA sequence in a control sample and respective DNA sequences in the identified subset in the control sample, determining differences in cycle threshold values for the target DNA sequence in an experimental sample and respective DNA sequences in the identified subset in the experimental sample, and comparing the differences.

Comparing the differences may include performing a statistical hypothesis test to conclude one of a statistically significant change exists between the control sample and the experimental sample for the target DNA sequence, and a statistically significant change does not exist between the control sample and the experimental sample for the target DNA sequence. Performing a statistical hypothesis test may include performing a T-test.

Performing a statistical analysis may include, for each of the target DNA sequences, tallying a DNA sequence score representative of a number of DNA sequences in the identified subset having a statistically significant difference in variation with respect to the respective target DNA sequence.

Determining the relative abundance of at least one of the target DNA sequences may include determining a fold change of a copy number of the target DNA sequence with respect to one or more normalizer DNA sequences.

The invention may include choosing a candidate DNA sequence to be one of the normalizer DNA sequences based on computing numerical criteria associated with a reproducibility of detection of the candidate DNA sequence across the samples.

Computing numerical criteria may includes determining sequences of numbers associated with relative quantities of the candidate DNA sequence with respect to respective other candidate DNA sequences across the samples, taking respective standard deviations of the sequences of numbers, and averaging the respective standard deviations.

The invention may include calculating a geometric mean of the numerical criteria of the normalizer DNA sequences, and using the geometric mean as a normalization factor for determining the fold change.

The invention may include choosing a DNA sequence to be the candidate DNA sequence based on it being in the identified subset of target DNA sequences.

One aspect of the invention is a rapid evaluative method employing DNA analysis on samples, comprising furnishing an array having a plurality of primers for detecting target DNA sequences, performing a genomic DNA detection process with the array to collect a reaction product dataset which includes data associated with the target DNA sequences, identifying a subset of the target DNA sequences to be used for comparison and normalization of the target DNA sequences, performing a statistical analysis of the reaction product data set by comparing data associated with the target DNA sequences to data associated with the identified subset of target DNA sequences, determining relative abundances of one or more of the target DNA sequences in at least one of the samples, and evaluating a subject using the relative abundances.

Performing a DNA detection process may include performing at least one of a DNA amplification process, a DNA signal detection process, and a DNA signal amplification process.

Performing a statistical analysis of the reaction product data set may include determining a statistically ranked list of a plurality of the target DNA sequences based on respective statistical variations of the data associated with the plurality of the target DNA sequences between control samples and experimental samples Evaluating a subject may include providing an evaluation and/or a diagnosis of a pathological condition. The pathological condition may cause variations in DNA sequence copy numbers of one or more indicator DNA sequences, and the invention may involve including at least one of the one or more indicator DNA sequences as a target DNA sequence.

Evaluating a subject may include monitoring the pathological condition. Evaluating a subject may include a staging of the pathological condition. The condition may be cancer. The cancer may result in a solid tumor, and the invention may include a sample taken from the tumor as one of the samples.

Evaluating may include evaluating and/or diagnosing at least one of a cancer resulting in a cystic tumor, a cancer resulting in a tumor including liquid, a cancer resulting in a metastasis, and a non-locally disseminated cancer within the subject.

The invention may include genes in the target DNA sequences. The invention may involve specifically choosing genes for the pathological condition being evaluated or diagnosed.

Furnishing an array may include providing a plurality of arrays having one or more control samples and one or more experimental samples.

The invention may include collecting the one or more control samples using a non-invasive procedure on the subject.

The invention may include taking at least one control sample and at least one experimental sample both from a single biopsy specimen.

Evaluating a subject may include evaluating at least one of a transgenic plant and a transgenic animal, wherein the target DNA sequences include genes added to a genome of the at least one of a transgenic plant and a transgenic animal.

Evaluating a subject may include selecting the at least one of a transgenic plant and a transgenic animal for participation in a reproductive process based on the evaluation.

Evaluating a subject may include evaluating an offspring for the presence of a heritable genetic condition, wherein the target DNA sequences include one or more genes whose copy numbers are indicative of the genetic condition.

In one aspect, the invention provides a method of identifying a set of DNA sequences whose variations are correlated with a pathological condition using DNA analysis on samples, including at least one sample derived from a subject with the pathological condition, comprising furnishing an array having a plurality of primers for detecting target DNA sequences, performing a genomic DNA detection process with the array to collect a reaction product dataset which includes data associated with the target DNA sequences, identifying a subset of the target DNA sequences to be used for comparison and normalization of the target DNA sequences, performing a statistically statistical analysis of the reaction product data set by comparing data associated with the target DNA sequences to data associated with the identified subset of target DNA sequences, determining a relative abundance of one or more of the target DNA sequences in at least one of the samples, and determining a correlated set of DNA sequences among the target DNA sequences whose variations have correlation with the pathological condition.

Determining a correlated set of DNA sequences may include determining a set of DNA sequences whose variations have correlation with a stage of the pathological condition, and the subject may be in the stage of the pathological condition.

The invention may include at least one of removing and adding DNA sequences to the correlated set of DNA sequences based on at least one of new data, and the subject progressing to a different stage of the pathological condition.

The DNA detection process may include at least one of a DNA amplification process, a DNA signal detection process, and a DNA signal amplification process.

Performing a statistical analysis of the reaction product data set may include providing a statistically ranked list of a plurality of the target DNA sequences based on respective copy numbers of the target DNA sequences. The pathological condition may be cancer. The invention may include genes in the target DNA sequences.

Furnishing an array may include providing a plurality of arrays having one or more control samples and one or more experimental samples.

The invention may include collecting the one or more control samples using a non-invasive procedure on the subject.

The invention may include adding the correlated set of DNA sequences to a predictive database of DNA sequences.

In one aspect, the invention provides for a rapid evaluative kit for evaluating or diagnosing a pathological condition in a subject, comprising an array having a plurality of primers for detecting target DNA sequences, DNA amplification and data collection means coupled to the array capable of collecting a reaction product dataset, which includes data associated with one or more specifically selected DNA sequences whose copy number variation is correlated with the existence of the pathological condition, and processing means to identify a subset of the target DNA sequences to be used for subsequent comparison and normalization of the selected DNA sequences, and provide a statistically ranked list of DNA sequences from which a relative abundance of the selected DNA sequences can be determined.

The invention may include a control sample and an experimental sample both collected from an anatomy of the subject.

BRIEF DESCRIPTION OF THE DRAWINGS

The foregoing and other objects and advantages of the invention will be appreciated more fully from the following further description thereof, with reference to the accompanying drawings wherein;

FIG. 2 displays a data entry sheet used with one embodiment of the system.

FIG. 4 depicts a normalization process for 96 DNA sequences.

FIG. 6 depicts a pattern recognition process consistent with the invention.

FIGS. 8a-b show the data sheet of FIG. 2 that is filled in with input data and shows results.

FIG. 9 shows an exemplary output sheet provided by the invention for displaying fold change information.

DESCRIPTION OF ILLUSTRATED EMBODIMENTS

To provide an overall understanding of the invention, certain illustrative embodiments will now be described. For purpose of clarity, the invention will be described largely with reference to QPCR methods for analyzing large arrays of DNA sequence data. However, it will be understood by one of ordinary skill in the art that the systems and methods described herein can be adapted and modified for other suitable applications and that such other additions and modifications will not depart from the scope hereof. Such applications include, but are not limited to, the analysis of microarrays, macroarrays, and protein arrays. For example, the systems and methods described herein have been adapted for performing microarray analysis of 25,000 DNA sequences or more. Other applications include the analysis of medical images to assess the level of disease progression and the effects of disease treatment. The techniques may also be used to analyze results from biometric recognition studies (e.g., finger printing). Those skilled in the art readily understand that numerous other applications are possible, such as the analysis of aerial and satellite photographs in general, and aspects of astro-photography in particular (e.g., to identify meteorites, comets, super novae, etc.).

Figure 1:
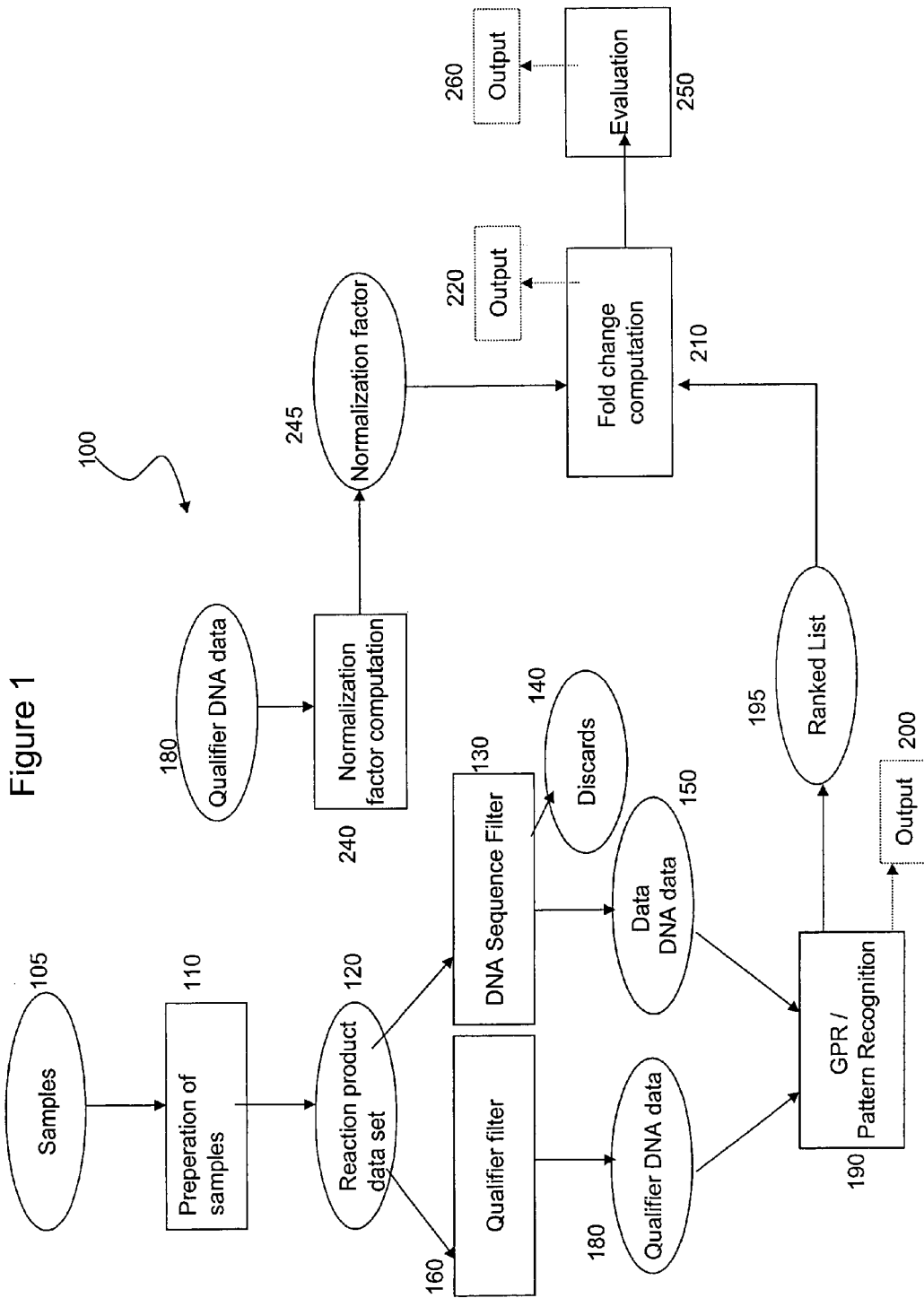
FIG. 1 depicts a block diagram of one process according to the invention.

Turning to FIG. 1, there is depicted a flow chart of one process 100 wherein an array, such as a microarray, of data is analyzed. The process 100 includes the steps of preparing 110 samples 105 (preferably including control samples and experimental samples). Preparing samples includes providing genomic DNA input in the array, and performing a DNA amplification or detection process to form a reaction product data set 120. The next steps are to perform a DNA sequence filtering step 130 to identify and discard non-informative data 140 while retaining informative DNA (also referred to as data DNA) data 150, and a qualifier filtering step 160 to identify qualifier DNA sequences 180 which will serve as a baseline for comparison and normalization in subsequent statistical analysis. The next step is to perform pattern recognition (GPR) 190 to output a ranked list 195 of DNA sequences based on their copy number variation in experimental samples when compared to control samples.

Additionally, the method includes performing a normalization factor computation step 240 which uses the qualifier DNA data set 180, mentioned above, as an input. The normalization factor computation 240 produces as an output a normalization factor 245, which is used in fold change computation step 210 to quantify the copy number change of certain DNA sequences in the reaction product data set in the experimental samples compared to the control samples. Finally, the method includes the step 250 of performing an evaluation. Steps 200, 220, and 260 may optionally provide for a graphical output to a user. Each of these steps will be discussed in detail below.

The systems and methods relate to the analysis of DNA sequences. In some embodiments, the DNA sequences are genes, in others the DNA sequences are within genes, and in others the DNA sequences do not comprise any particular gene. It is to be understood in this application that certain embodiments may be discussed in the context of genes but are equally applicable for the case of DNA sequences in general.

Preparation of Samples for Analysis 110

In one practice, the methods described herein use genomic DNA as the source for subsequent DNA analysis. The use of genomic DNA is in contrast to the use of gene expression inputs, such as cDNA. Typical methods that employ gene expression inputs require the step of providing and purifying mRNA and synthesizing associated cDNA. The disclosed method simplifies pre-processing by employing DNA directly from the samples without the need for cDNA synthesis. The genomic DNA may be derived from samples 105 from any suitable DNA source, such as a person, plant, or animal.

The samples 105 include control samples and experimental samples. Experimental samples are generally taken from a subject with a condition of interest, and control samples are generally taken from a subject without the condition of interest. Typically, experimental samples are taken from a diseased patient, and control samples are taken from a healthy patient. Alternatively, the experimental samples may be taken from a diseased patient and the control samples can be taken from a healthy part of the same patient. A subject can be, for example, a human, animal, or plant. Control and/or experimental samples 105 can be derived using a biopsy, such as an incisional biopsy, a core biopsy, an excisional biopsy, or a needle aspiration biopsy. Gathering a biopsy specimen includes the removal and/or examination of tissue, cells, fluids, and/or other materials from a body of a subject.

Alternatively, the control samples 105 may be taken using a non-invasive procedure such as a scrape or swab. For example, the system may employ a cheek swab to collect a sample that contains DNA.

Varying numbers of control and experimental samples can be used. In one practice, at least three control samples and at least three experimental samples are used. Some of the discussion below will illustratively discuss the invention in the context of having three control samples and three experimental samples processed on a plurality of arrays, but other quantities are consistent with the invention. In the discussion below, each of the control samples are replicates of each other. Replicates refer to samples that are related to each other in the context of the particular application. By way of example, the replicates may be biological replicates, in that they are different samples taken from the same subject. However, they may also be technical replicates, in that the method is performed several times on the same DNA sample and the resultant data constitute the replicates required for the data input. Similarly, in the discussion below, the experimental samples are replicates of each other.

As discussed above, the DNA sequences may be provided using one or more arrays. A set of target DNA sequences are identified for examination. The one or more arrays are provided with array primers for processing the target DNA sequences (i.e., oligonucleotide primers capable of amplifying the target DNA sequences).

In some embodiments, each of the plurality of samples/ replicates is processed on its own respective array. The number of DNA sequences that can be processed will be discussed below. In preferred embodiments, each array may allow analysis of 384 or 96 DNA sequences.

The analysis described below is performed on a set of prescribed DNA sequences taken from one or more samples that undergo a DNA detection process. The DNA detection process can include a DNA amplification process, a DNA signal detection process, a DNA signal amplification process, or combinations thereof. Exemplary amplification/detection processes include rolling circle amplification, Invader assay, helicase-dependent amplification, karyotyping, FISH, southern blotting, PCR-based methods such as QPCR, or other methods known in the art. The amplification process may be isothermal or non-isothermal. Instead of or in addition to the DNA amplification process, a DNA signal detection or DNA signal amplification process may be used.

FIGS. 8*a-b* and FIG. 9 show a portion of a list of genes with data included in a reaction product data set. The reaction product data set of FIGS. 8*a-b* and FIG. 9 includes data from 384 genes, although only a subset of the data are shown in the screen captures of the figures. The experimental sample replicates, also referred to as group 2 replicates, were derived from genomic DNA taken from a tumor of a single C57BI/6J strain mouse that was excised and determined to be a B-cell lymphoma. The control replicates, also referred to as group 1 replicates, were derived from genomic DNA taken from a C57BI/6J (strain-matched) mouse. FIGS. 8*a-b* and 9 and the data and results therein will be used in the following descriptions as an illustrative embodiment.

Reaction Product Dataset 120

The target DNA sequences (i.e., the specific DNA sequences to be analyzed) can be predefined by a user. Processing steps, including the preparation of samples 110 discussed above, generate a reaction product data set 120 that includes data associated with the target DNA sequences in the samples. Data included in a reaction product data set generally can include data associated with respective amplification activities of the target DNA sequences. In one practice, the reaction product data set includes cycle threshold (CT) values for the target DNA sequences. The DNA sequences chosen for inclusion as target DNA sequences can be predefined and customized for particular applications, such as for cancer diagnosis.

DNA Sequence Filter 130

Referring back to FIG. 1, the reaction product data set is processed by a DNA sequence filter 130. The DNA sequence filter 130 separates the DNA sequences in the reaction product data set into a set of data DNA sequences whose data 150 is identified for further analysis, and a set of non-informative or "discard" DNA sequences whose data 140 is to be discarded. In one practice, the DNA sequence filter 130, as well as the qualifier filter 160 and the GPR pattern recognition 190 to be discussed below, can be implemented as a software-based process. As used herein, target DNA sequences whose data is not discarded by the DNA sequence filter 130, discussed below, are referred to as 'data DNA sequences.'

The non-informative DNA sequences include sequences whose portion 140 of the array data seems to lack integrity and therefore may interfere with obtaining proper results. This may happen when, for example, a PCR or other amplification/detection process fails to take hold, and does not properly amplify or accurately detect the material. This may also happen due to human or computer errors.

Figure 3:
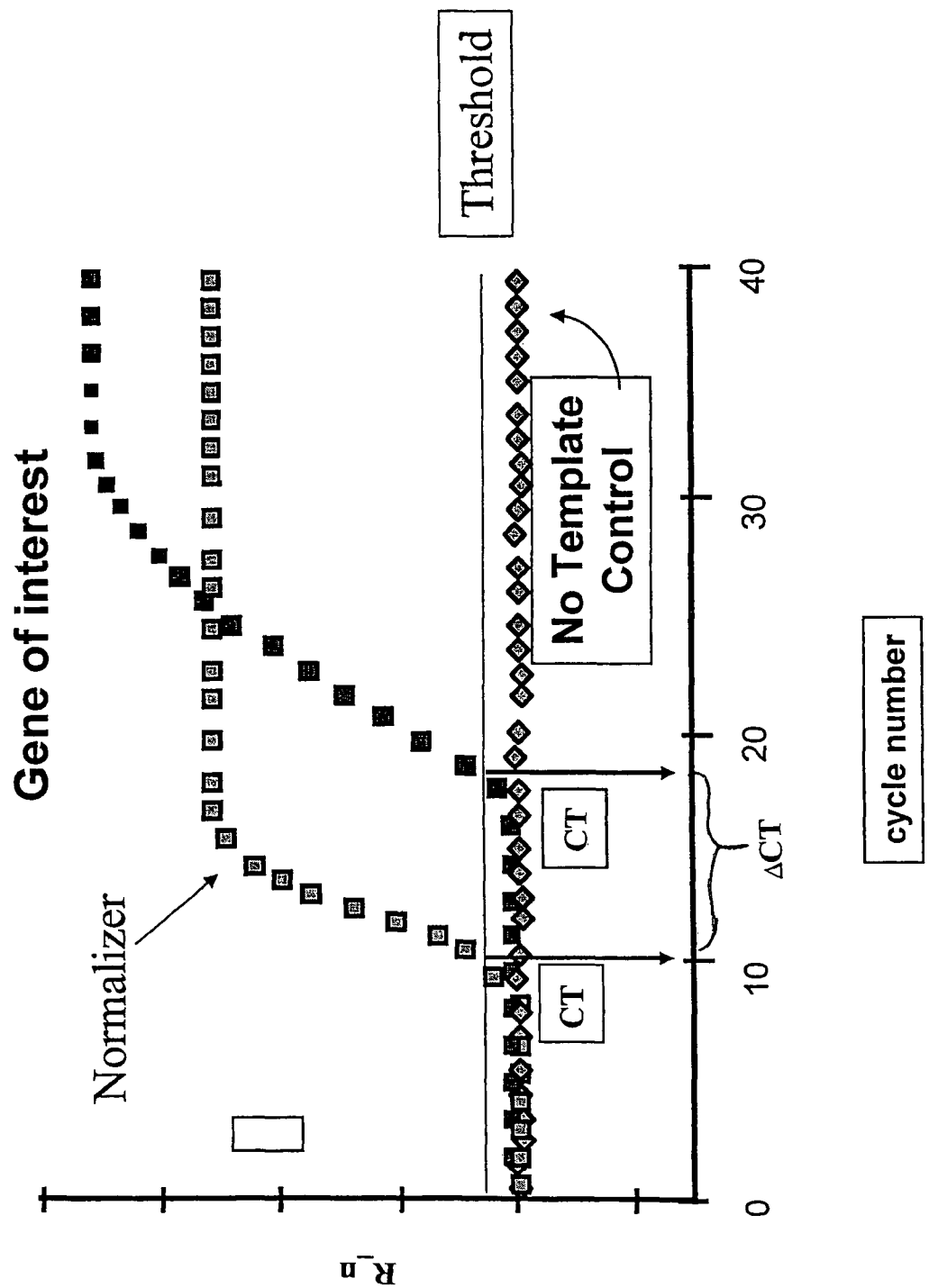
FIG. 3 depicts an amplification and subsequent DNA sequence normalization process.

The DNA sequence filter 130, as well as the qualifier filter 160 and the GPR pattern recognition 190 to be discussed below, uses Cycle Cutoff (CC) values and Cycle Threshold (CT) values. A CT value for a particular DNA sequence is the PCR cycle number at which the relative florescence ($R\_n$) of that DNA sequence exceeds a prescribed threshold. FIG. 3 illustrates the CT values for two genes. The data recorded for each DNA sequence in each replicate includes its CT value.

A CC value is generally a user-defined parameter used to identify genomic data that is to be discarded. More specifically, the CC is the PCR cycle number above which data from a particular DNA sequence will be disregarded if that DNA sequence's $R\_n$ has not exceeded the prescribed threshold. In other words, a DNA sequence's data is discarded if CT>CC for that DNA sequence. Preferred CC values are between about 36 cycles and about 42 cycles, since after about this many cycles, stochastic amplification of low copy-number targets can lead to large variability in the data. Consequently, using the CC as a cutoff eliminates this noisy data. Other preferred cycle cutoff values include 38 and 38.5, and are typically less than 40. In FIG. 8*a*, the cycle cutoff is set to 37.5 as indicated by the cell 275 marked "cycle cutoff." The cycle cutoff may be set to a default fixed value, or it may be set to any desired value according to a user input, such as the Cycle cutoff cell in FIG. 8*a*.

Data associated with a DNA sequence passes through the DNA sequence filter 130 if, in one practice, all observations in either the control group (group 1) or the experimental group (group 2) fall below the cycle cutoff value. The following truth table, Table 1, describes output of the DNA sequence filter:

TABLE 1

| ALL control data (group 1) ≦CC | ALL experimental data (group 2) ≦CC | Output |
| --- | --- | --- |
| True | True | True |
| False | True | True |
| True | False | True |
| False | False | False |

Thus, GPR will consider data from a DNA sequence for further analysis if it is well represented in either control or experimental groups (or both), but will disregard data from a DNA sequence if it not well represented ('off') in both groups. Other embodiments, however, may disregard data from a DNA sequence under more stringent or less stringent criteria, such as if any control data and any experimental data exceed the CC value, if any control data or any experimental data exceed the CC value, or if a majority of control data and/or a majority of experimental data exceed the CC value. As used herein, a DNA sequence exceeding the CC value refers to a DNA sequence whose $R\_n$ has not exceeded the prescribed threshold after CC cycles; i.e., a DNA sequence for which CT>CC.

FIG. 8*b* shows a list of DNA sequences in a reaction product data set, and displays the results of the DNA sequence filter under the column titled "Data Gene?" In this implementation, if CT>40 for a DNA sequence, then its CT value is recorded as 40. The reaction product data set in this example includes data from 384 DNA sequences, although only about 40 are shown in the figure. The control group is designated as 'Group 1' and the experimental group is designated as 'Group 2'. In this instance, gene #B06 has one group 1 replicate with a CT of about 39.38927 as shown in FIG. 8*a*, which is greater than the CC of 37.5. In addition, all replicates in group 2 have a CT that is greater than 37.5. Therefore, this gene is not passed through the DNA sequence filter. This is indicated by the "False" in the corresponding entry in the "Data Gene" column. In this example, there were 381 data genes out of the 384 genes examined, as indicated by "Data Genes" cell in FIG. 9.

While the above described embodiment of the DNA sequence filter is discussed in the context of Cycle Cutoff and Cycle Threshold values in a PCR-based amplification process, other embodiments may use other amplification methods and/or criteria for DNA sequence filtering. The appropriate criteria for DNA sequence filtering used will of course depend on the application at hand or the amplification/detection method used.

Qualifier Filter 160

The depicted process in FIG. 1 includes a qualifier filter 160. The qualifier filter 160 processes data to identify DNA sequences 180 that may be suitable for use as qualifiers based at least in part on their respective amplification activities. Data from DNA sequences 180 identified as qualifiers will serve in later steps as a baseline for comparison/normalization for statistical analysis; data from undiscarded data DNA sequences 150 will be statistically compared and normalized against data from each of the qualifier DNA sequences 180. Thus, the set of qualifier DNA sequences generally refers to a subset of the target DNA sequences whose data will be used in comparison and normalization of the target DNA sequences. Amplification activity generally refers to characteristics of the results/data obtained from the target DNA sequences during the amplification/detection processes mentioned above.

The qualifier filter filters data into overlapping data DNA sequence and qualifier DNA sequence groups. Data from a DNA sequence passes through the qualifier filter 160 if, in one process, all observations in both control and experimental groups fall below the cycle cutoff value. The following truth table, Table 2, describes output of the qualifier filter:

TABLE 2

| ALL control data (group1) ≦CC | ALL experimental data (group2) ≦CC | Output |
| --- | --- | --- |
| True | True | True |
| False | True | False |
| True | False | False |
| False | False | False |

Thus, GPR will consider a DNA sequence as a candidate qualifier on the conditions that it is well represented in both control and experimental groups, but will disregard a DNA sequence if it not well represented ('off') in either group. This ensures that only DNA sequences that have measurable copy numbers in both groups are used as qualifiers and that DNA sequences that may be off (CT>CC) are not considered as qualifiers (these DNA sequences may still be included in the data DNA sequence set). Note that by comparing Table 1 and Table 2, it is evident that the set of qualified DNA sequences is in this practice necessarily a subset of the data DNA sequences. However, as was the case with the DNA sequence filter described above, more stringent or less stringent criteria may be used for identifying potential qualifier DNA sequences.

By way of illustration, FIG. 8b displays the results of the qualifier filter 160 under the column titled "Qualifier?" As shown in FIG. 8a, gene # A18 (Hoxa11) has a Group 2 replicate with a CT value of 37.574883, which is greater than the CT value of 37.5. Therefore, this gene is disqualified for use as a qualifier as indicated by the "False" in the corresponding cell under the "Qualifier?" column. Similarly, gene #'s B03, B04, B05, B06, and B07 have at least one replicate with a CT value greater than 37.5, so their data is not passed by the qualifier filter. In this example, there were 372 qualifier genes out of the 384 genes examined, as indicated by the "Qualifiers" cell in FIG. 9.

While the above described embodiment of the DNA sequence filter is discussed in the context of Cycle Cutoff values in a PCR-based amplification process, other embodiments may use other amplification methods and/or criteria for DNA sequence filtering. The appropriate criteria for DNA sequence filtering used will of course depend on the application at hand or the amplification/detection method used.

Global Pattern Recognition 190

Data associated with the data DNA sequences 150, including data associated with the qualifier DNA sequences 180, is passed to the "GPR" pattern recognition process 190 which performs a statistical analysis of the reaction product dataset and identifies those DNA sequences in the array whose copy numbers have varied in a statistically significant manner in the experimental samples when compared to the control samples.

In one practice, for each dataset (i.e. column of 384 CT values), GPR takes data from each data DNA sequence in the set 150 and compares/normalizes it to data from each eligible qualifier in the set 180 in succession to generate a sequence of $\Delta CT$ values. An exemplary normalization method involves subtraction, as follows: $\Delta CT_{Data\ DNA\ sequence} = CT_{Data\ DNA\ sequence} - CT_{Qualifier}$. This is depicted graphically in FIG. 3. In particular, FIG. 3 shows the relative florescence R_n of a qualifier DNA sequence as well as a DNA sequence of interest. More specifically, FIG. 3 shows a graph wherein the cycle numbers are set out along the X-axis and the relative florescences set out along the Y-axis. The R_n values for the qualifier DNA sequence and the DNA sequence of interest are shown as plots on this graph and a cycle threshold line is indicated. The difference between cutoff thresholds is shown in FIG. 3 by $\Delta Ct$ and in FIG. 3 this is difference is approximately 8 cycles.

As shown in FIG. 4, the $\Delta CT$ values for each DNA sequence of interest is generated. For each DNA sequence/qualifier combination, the $\Delta C_T$ values generated for the control and experimental groups are compared by a two-tailed heteroscedastic (unpaired) Student's T-test and a 'hit' is recorded if the p-value from the T-test is below a user-defined threshold alpha value. In FIG. 8a, alpha is set to 0.05, as indicated in the cell marked "alpha." Other values can be used, and a lower alpha results in a more stringent criteria for marking a 'hit.'

Figure 5:
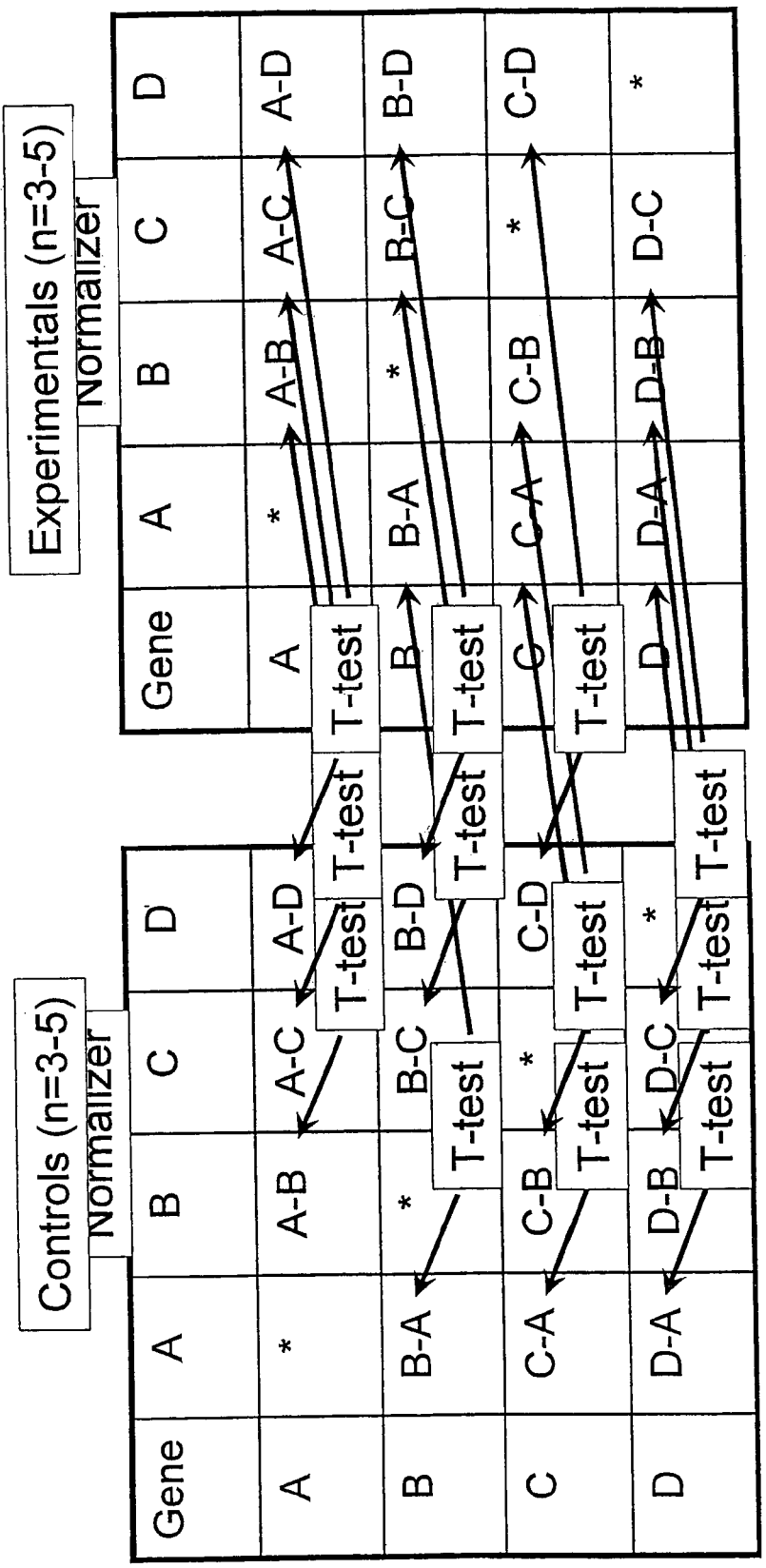
FIG. 5 depicts a pattern detection process consistent with the invention.

The process for implementing the pattern recognition analysis is depicted graphically in FIG. 5. Specifically, FIG. 5 illustrates that for each data DNA sequence/qualifier combination the $\Delta CT$ values generated for the control and experimental groups are compared. In the embodiment depicted by FIG. 5, each of these combinations is compared by the T-test. The T-test allows the researcher to make a hypothesis as to whether a statistically significant variation occurred between the control data and the experimental data. In this way, the comparisons being made may determine which of the DNA sequence/qualifier combinations appear to have varied in a statistically significant manner. While this exemplary embodiment is described in the context of a Student's T-test using a threshold for the p-values, this is not necessary for the invention. Other statistical hypothesis testing methods known in the art, namely, methods which choose one hypothesis from among a set of hypotheses based on observed sample data and a probabilistic model, may be used. Typically, a binary hypothesis testing method is used. The T-test has at least the benefit of being well known, especially suited to small sample numbers of samples (i.e., fewer than 25), and incorporated as a function in Microsoft Excel.

GPR provides an experiment-independent score for each DNA sequence related to the significance of its statistical change. To this end, each time a significant variation is detected, a hit is recorded for that data DNA sequence. This is depicted graphically in FIG. 6 which shows the data DNA sequence-qualifier combinations earlier presented in FIG. 5. For each data DNA sequence/qualifier combination an indication is recorded as to whether the T-test indicated a statistically significant variation between experimental data and control data (based on the user defined alpha threshold). For each data DNA sequence, the number of hits identified is added and recorded. This is shown in FIG. 6 under the "# hits" column. In this case, the DNA sequence A records only one significant hit. That hit occurred for the DNA sequence qualifier combination A-C. In contrast, the DNA sequence B records three significant hits for the DNA sequence qualifier combinations B-A, B-C, and B-D.

After recording the hits, GPR, in one practice, tallies the hits for each DNA sequence with data in the set 150 against all eligible qualifiers with data in the set 180 and ranks the DNA sequences in descending order of number of hits. The experiment-independent DNA sequence score is obtained by dividing the number of hits for a DNA sequence by the total number of eligible qualifiers. Using the example of FIGS. 8a-b and 9, the gene Tsg101 had 370 hits (shown in the "# Total hits" column in FIG. 9) out of the 372 qualifier genes, resulting in a score of about 0.995, which is listed under the "Score" column.

The DNA sequences with the highest scores have changed most significantly in the dataset. DNA sequences whose data failed to pass through the DNA sequence filter are, in one embodiment, assigned –1 hits and a "N.S." (not significant) in the score column and are ranked alphabetically at the bottom of the output page (increasing the CC usually makes more of these DNA sequences 'significant').

Other methods for determining the score for each of the DNA sequences are envisioned. Methods may include weighting a 'hit' differently depending on which qualifier DNA sequence the 'hit' is with respect to, and measuring the "quality" of a qualifier to determine the weightings. Some methods for measuring the quality of a qualifier will be discussed below in the context of choosing normalizer DNA sequences in the normalization factor computation step 240. 'Hits' may also be weighted based on the extent of the magnitude difference between the p-value of a particular DNA sequence and the alpha threshold criteria of the T-test.

The multiple DNA sequence normalization described above makes no pre-supposition about the constant level of a particular qualifier. After filtering the data, GPR normalizes data from each eligible DNA sequence against data from every other DNA sequence that is eligible as a qualifier. Since GPR considers each DNA sequence individually, it is not as adversely affected by PCR dropouts. Because it employs replicate sampling, GPR determines significance based on replicate consistency rather than by the magnitude of fold changes. Thus consistent small fold changes even in biologically important DNA sequences, such as transcription factors would be detected.

Figure 2:
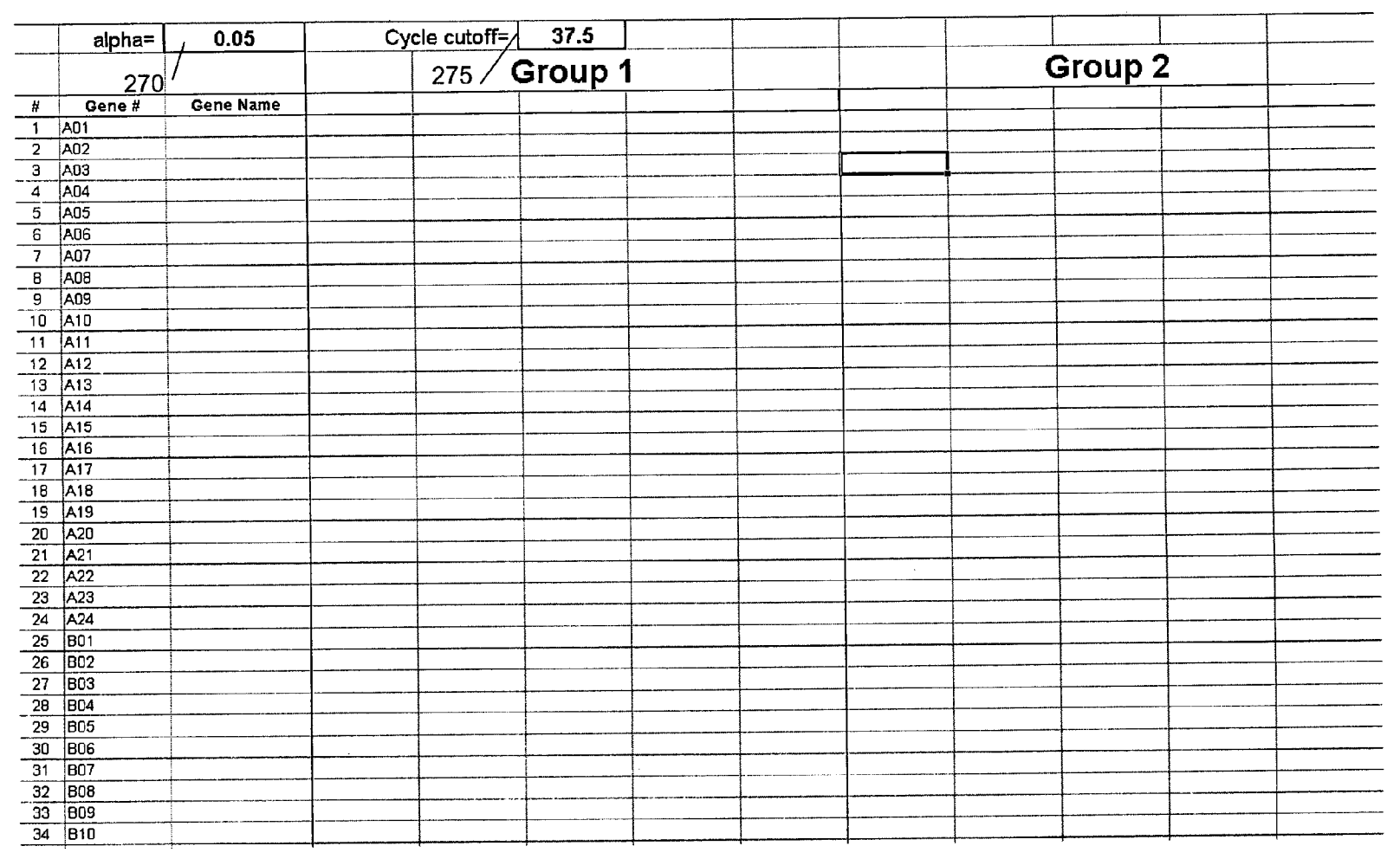

We now discuss a process for performing the steps described thus far with reference to FIG. 2, which is the data entry sheet used to produce the results of FIGS. 8a-b and 9. The process is initiated by entering DNA sequence names for the targets in the 'Gene Name' column. The user may enter up to 384 CT values for up to five biological replicates in the two comparison groups.

After entering CT values and DNA sequence names and running the program, the program displays an output 200 provided by the system, such as the output depicted in FIG. 9. The output includes the reaction product data set and includes the ranked list 195 of FIG. 1 in the "Gene" column (rankings are shown in the "Rank" column), as well as the results of the fold change computation, to be discussed below, in the "*Fold Change with respect to 10 best normalizers" column. With reference to FIGS. 2 and 9, processing steps may include:

1. On the sheet illustrated in FIG. 2, enter the desired alpha threshold for significance cutoff (for the T-test of $\Delta$CT values) and the Cycle Cutoff in the appropriate cells 270 and 275 respectively.
2. Click a 'Run GPR' button (not shown). The algorithm subsequently runs and automatically switches to an output sheet (FIG. 9) with the results.
3. Optionally, the dataset can be saved as a separate file by pressing a 'Save results in a separate file' button (not shown).

The page can be setup to print the entire GPR output sheet onto one sheet.

The ranked list in this embodiment is related to the number of hits, as mentioned above. However, the ranking may be based on other measures. In general, the ranked list will be produced based on rankings dependent upon some measure of the statistical variations of the data associated with the plurality of the ranked target DNA sequences between the experimental samples and the control samples.

Normalizer Factor Computation 240 and Fold Change Computation 210

As depicted in FIGS. 1 and 9, the GPR step 190 produces a ranked list of DNA sequences identified as having statistically significant copy number changes. The rankings, as illustrated in FIG. 9, are based on the score from the GPR step 190. This ranked list is then mapped to a measure of the relative abundance of the DNA sequences identified as having statistically significant copy number changes. FIG. 9 shows the quantification of the relative abundance given as a fold change; however, other numerical metrics associated with a genomic DNA copy number may be used. The fold change is related to the multiple of increase or decrease of a particular DNA sequence in the experimental samples compared to the control samples.

Figure 7B:
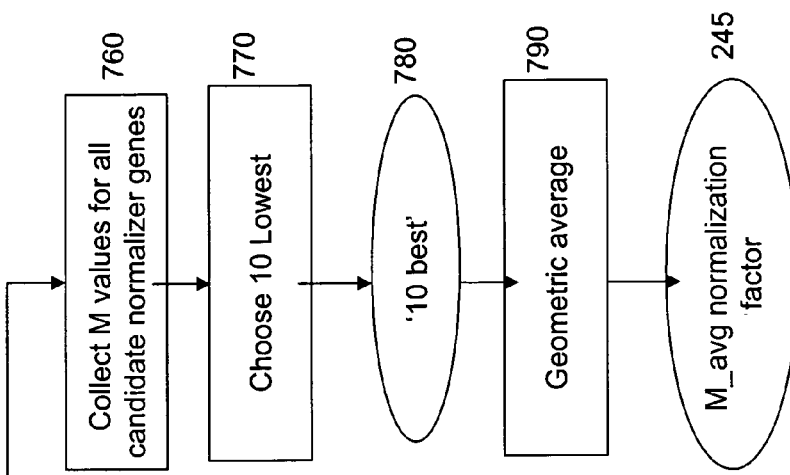
FIGS. 7a-b depict a block diagram of the normalization factor computation 240 of FIG. 1.
Figure 7A:
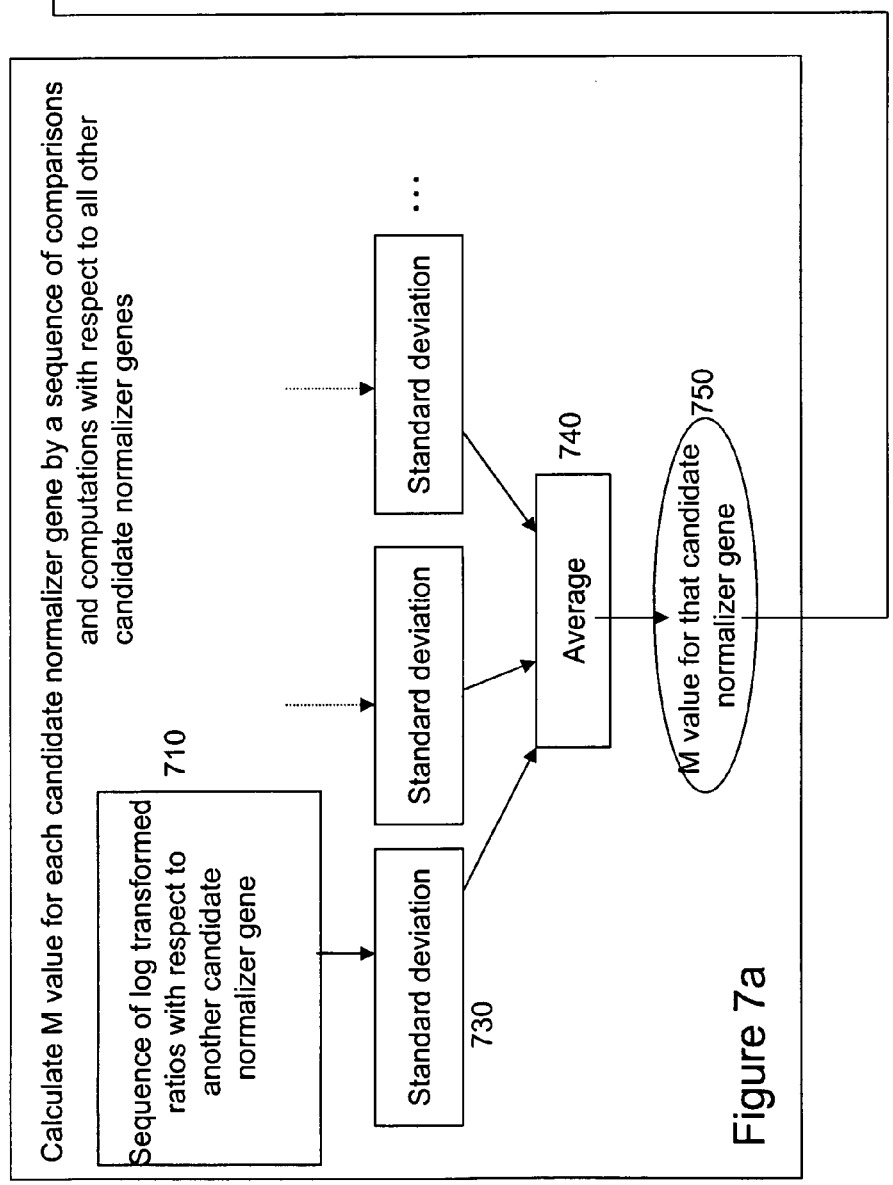

The fold change is computed with respect to a normalization factor 245, which is associated with one or more normalizers. The process for computing the normalization factor 245 is depicted in FIGS. 7a and 7b. Normalizers refer to DNA sequences whose data may be used as a baseline for comparison and/or normalization of data associated with DNA sequences with data in the reaction product data set 120.

With reference to FIGS. 1 and 7, the fold change is computed with respect to a set of normalizers 780 identified in a normalization factor computation step 240 as suitable normalizers. In FIG. 7B, the normalization factor is computed with respect to a set of 10 normalizers referred to as the '10 best' normalizers 780.

More specifically, the process begins with data from a set of candidate normalizer DNA sequences. Candidate normalizer DNA sequences generally refer to the set of DNA sequences that are considered as possible normalizer DNA sequences. Various subsets of the target DNA sequences, or all of the target DNA sequences, can be candidate normalizer DNA sequences.

However, in this embodiment, the candidate normalizer DNA sequences are the set of qualifier DNA sequences as identified by the qualifier filter 160. DNA sequences are chosen to be in the '10 best' set 780 based on a measure of their reproducibility of detection across samples. Reproducibility of detection across samples for a given DNA sequence generally refers to a level of uniformity/reproducibility of detection results for that DNA sequence when amplification/detection processes are performed for the DNA sequence for multiple samples.

In particular, the method compares data from each candidate normalizer DNA sequence (i.e., each DNA sequence with data in the set 180) with data from each other candidate normalizer DNA sequence in the set 180 to determine a numerical measure, called an M value 750, for each candidate normalizer DNA sequence. The M value 750 is representative of its reproducibility of detection across samples.

More specifically, the method includes, for each candidate normalizer DNA sequence, determining a sequence of numbers associated with the relative quantity of that candidate DNA sequence with respect to another candidate DNA sequence for each of the samples. In this embodiment, the sequence of numbers includes the log (base 2) transformed ratios 710 of that DNA sequence's CT value with respect to another candidate normalizer DNA sequence's CT value for each of the samples. The standard deviation 730 of this sequence is computed. Such a standard deviation is computed for this candidate DNA sequence with respect to each of the other candidate DNA sequences, and the resulting standard deviations are averaged 740. This average is the DNA sequence-stability measure M 750 for that candidate normalizer. After the M value for each candidate is collected 760, the candidates with the ten lowest M-values are chosen 770 to be in the '10 best' set 780. The M measures for the ten DNA sequences with the ten lowest M measures are geometrically averaged 790 to arrive at the normalization factor M_avg 245 used as the basis to compute the fold changes in step 210 for the GPR-ranked DNA sequences.

In alternate embodiments, a log transform is not taken. Instead of computing the log transformed ratios of CT values in step 710, the $\Delta$CT value for the DNA sequence with respect to another candidate normalizer DNA sequence is used. Still other embodiments may use other methods for determining a numerical criteria associated with the reproducibility of detection across samples of the candidate normalizer DNA sequences. The other methods can use CT values as those described above, or other numerical and measurable quantities associated with their copy numbers in the respective samples.

Alternately, the method may use more or less than ten DNA sequences in the normalizer set. In some embodiments, the method may involve iteratively eliminating DNA sequences from the set based in part on their respective M values and the M_avg value of the DNA sequences remaining in the set. The M value described is one illustrative example, and other measures of sample variance known in the art may be used. Additionally, alternate methods, including alternate averaging methods such as arithmetic averaging, for aggregating the M values of the candidates into a single factor M_avg may be used.

An output 220 displays the fold change results, as illustrated in FIG. 9 under the heading "*Fold change with respect to 10 best normalizers," along with other relevant information. The information displayed includes the alpha value, CT values of DNA sequences in the control and experimental samples, the CC value, p-value results from the T-tests, results from the DNA sequence filter, results from the normalization factor computation, DNA sequence identification information, the numbers of control/healthy and experimental/sick samples, the number of 'hits' for each DNA sequence, the DNA sequence's GPR rank, and the DNA sequence's fold change.

Evaluation 250

In one aspect, as shown in FIG. 1, the method maps a fold change output from the fold change computation step 210, such as the fold change output in FIG. 9, to an evaluation 250. In general, the evaluation can be a copy number analysis based on the fold change computation 210. Thus, as will be discussed below, the invention provides for a rapid evaluative method employing genomic DNA analysis.

Pathological Conditions

In one aspect, the evaluation includes a diagnosis of a pathological condition, such as cancer. Pathological conditions may include conditions of or relating to pathology, including conditions resulting in an alteration of the anatomy caused by disease. Anatomy may include any structural or physical makeup or arrangement of, for example, an organism and/or its parts.

In some embodiments, specific DNA sequences are chosen to be in the reaction product data set based on a priori knowledge of their correlation with the presence of cancer. These DNA sequences are generally referred to as indicator DNA sequences. Correlation between a pathological condition and a particular DNA sequence includes any causal and/or mutual relationship between the DNA sequence, its copy number, or other characteristics associated therewith and the pathological condition. Other methods for choosing DNA sequences may also be used. For example, if a particular gene is known to have correlation to the existence of a pathological condition, then genes located in the same chromosomal region can be included.

To evaluate a subject, control, or "Group 1," and experimental, or "Group 2," samples are collected or furnished using methods described with relation to the preparation of samples step 110. Control samples are generally taken from a known healthy subject, while experimental samples are generally taken from a potentially diseased subject. In one practice, if the upregulation of an indicator DNA sequence by a particular amount is known to be indicative of a particular pathological condition, and the GPR step, in its ranked list, indicates that the indicator DNA sequence has been upregulated, its fold-change can be examined to determine the degree of change in that DNA sequence's copy number in the experimental samples compared to the control samples. If this amount of change is consistent with the pathological condition being examined, the result of the evaluation is a determination that the condition being examined is present in the experimental samples. In this case, in one embodiment, a 'positive' diagnosis is made.

In alternate practices, more than one DNA sequence is used as a basis for evaluation. A pathological condition may result in a general characteristic DNA sequence profile pattern across a larger set of DNA sequences. Since the present invention can efficiently handle large arrays of DNA sequences, this set of DNA sequences may be chosen as target DNA sequences and have associated data included as elements of the reaction product data set, and the resulting fold-change quantification of those DNA sequences can be used to pattern-match to the pathological condition's characteristic DNA sequence profile pattern.

The systems and methods described herein are understood as particularly effective for this purpose since the statistical significance of copy number changes as reported by GPR 190 is uneffected by the magnitude of copy number change. Certain pathological conditions may consistently and causally result in copy number changes of particular DNA sequences, but this change may consistently be in small amounts. While it is conceivable that the most significant DNA sequences are the ones whose copy numbers have changed dramatically, it is also possible that a small, reproducible change in other DNA sequences may have substantial biological significance. Unlike many methods known in the art, such as standard microarray and PCR-based techniques, the methods described herein are sensitive to this.

In addition to determining the presence of a pathological condition, such as cancer, the method can be used to monitor or stage pathological conditions. Staging a pathological condition generally refers to providing a categorization of the extent to which a pathological condition has advanced. Monitoring a pathological condition generally refers to observing the progress of the pathological condition over time, such as observing its progression through stages. For example, stages for cancer may include Stage 0, in which cancers are in situ lesions that have not spread to other sites; Stage I, in which the cancer is locally limited to a tissue or organ near its origin; Stage II, in which there is limited spread; Stage III, in which there is extensive regional spreading; and Stage IV, in which the cancer has metastasized to non-local parts of the anatomy. Other cancer staging methods can also be used. Since various stages of pathological conditions may give rise to distinct copy number variations for a particular set of DNA sequences, these DNA sequences can be included in the reaction data product set. A diagnostic clinician can determine which stage of the pathological condition is most consistent with the observed fold changes. Alternately, each stage of the pathological condition may be associated with a different set of DNA sequences. In this case, the methods can be employed with each of these sets of DNA sequences. The diagnostic clinician can examine the fold change results for each of the DNA sequence sets and determine which stage of the condition is most consistent with the observed fold changes.

In addition to determining the presence of a condition and staging the condition, the invention can be used to monitor a condition. By repeating the methods of the invention over time and observing how particular DNA sequence copy numbers are varying temporally, a diagnostic clinician can monitor the progress of a patient, and this may help to determine the efficacy of the patient's treatment, and may help determine appropriate future courses of treatment.

As mentioned above, the invention is conducive for clinical use because it simplifies the gathering and preprocessing of samples for evaluative/diagnostic purposes at least in part because the invention makes use of genomic DNA as opposed to gene expression products. This eliminates steps such as purifying RNA and synthesizing cDNA, which in part allows a diagnostic clinician to collect samples using simple and, for the case of control samples, possibly non-invasive methods. For example, in cancer diagnosis, an experimental sample can be derived from tumor cells, and a control cell can be derived from a routine cheek swab. Non-invasive procedures generally include any procedure which requires little or substantially no entry into a body of a patient. In particular, non-invasive techniques require no incision or insertion of an instrument into a body.

Because of the simplified preprocessing and the use of detection methods which require smaller samples, a clinician can use relatively small samples. It may be possible to obtain a sufficient number of technical or even biological replicates for a complete diagnostic process from a single biopsy specimen which includes both diseased and normal cells. In this case, the diseased cells are isolated by cutting or otherwise separating a sick portion of the biopsy specimen from a healthy portion. Because of the simple processing, this application is particularly well suited to test for cancers with solid tumors, wherein the experimental sample is directly taken from the tumor itself. The invention can be used for other cancer types as will be discussed below.

The step of evaluation includes observing fold changes of particular DNA sequences in an experimental sample compared to a control sample, and determining which pathological condition or stage of a pathological condition is consistent with the observations. This determination may be qualitative in nature, drawing on the experience of a professional. However, it may also be quantitative and automated. In this case, the process makes use of pattern recognition methods to recognize DNA sequence profile patterns consistent with the pathological condition/stage under investigation. For example, if being used to determine between the presence and non-presence of a pathological condition, it may employ hypothesis testing methods using the fold change data as an input. If being used to determine to which stage among M stages a particular pathological condition has progressed, it may employ M-ary hypothesis testing methods. The automated process can be software based.

After the evaluation, a software-based system may provide an output 260 to a user. The output can display the results of the evaluation on a graphical interface.

Genetic Evaluation

In another aspect, the evaluation can be an evaluation of a heritable genetic condition, such as genetic deletions or amplifications which result in genetic disorders. Such conditions can be diagnosed prenatally, for example, by analysis of DNA from amniotic fluid, or postnatally, for example, from a biopsy of the newborn. In this aspect, a particular DNA sequence to be investigated for deletion and/or amplification is included as a target DNA sequence, and its data is recorded in the reaction product data set 120. Experimental samples are taken using, for example, one of the prenatal or postnatal methods described above. Control samples are taken from a parent afflicted with the heritable genetic condition using any of the methods described herein, such as a tissue biopsy. The statistical variation and/or fold-change of the DNA sequence to be investigated is determined using the methods described herein.

Transgenic Plants or Animals

In another aspect, the evaluation is an evaluation of a transgenic plant. In particular, a transgenic plant refers to a plant that has been genetically reengineered by, for example, adding one or more genes to the plant's genome. The added genes, referred to as transgenes, may improve one or more characteristics of the plant, such as its disease resistance, herbicide resistance, pest resistance, yield, and/or longevity. In such cases, it is desirable to identify and reproduce transgenic plants from among a set of transgenic plants based on their having desirable levels of transgene copy number levels. In one aspect, this invention takes samples derived from a transgenic plant as experimental replicates, and samples derived from a corresponding plant (i.e., a plant of the same species) as the control replicates. The steps of the invention discussed above are performed, and then repeated for each transgenic plant using the same control plant. Finally, those transgenic plants that demonstrated the most desirable transgene variation as indicated by one or both of the ranked lists 195 or the fold change outputs 220 are selected for reproduction.

The same method is generally followed for transgene analysis and/or selective reproduction of transgenic animals.

Creating Custom DNA Sequence Sets

Figure 10:
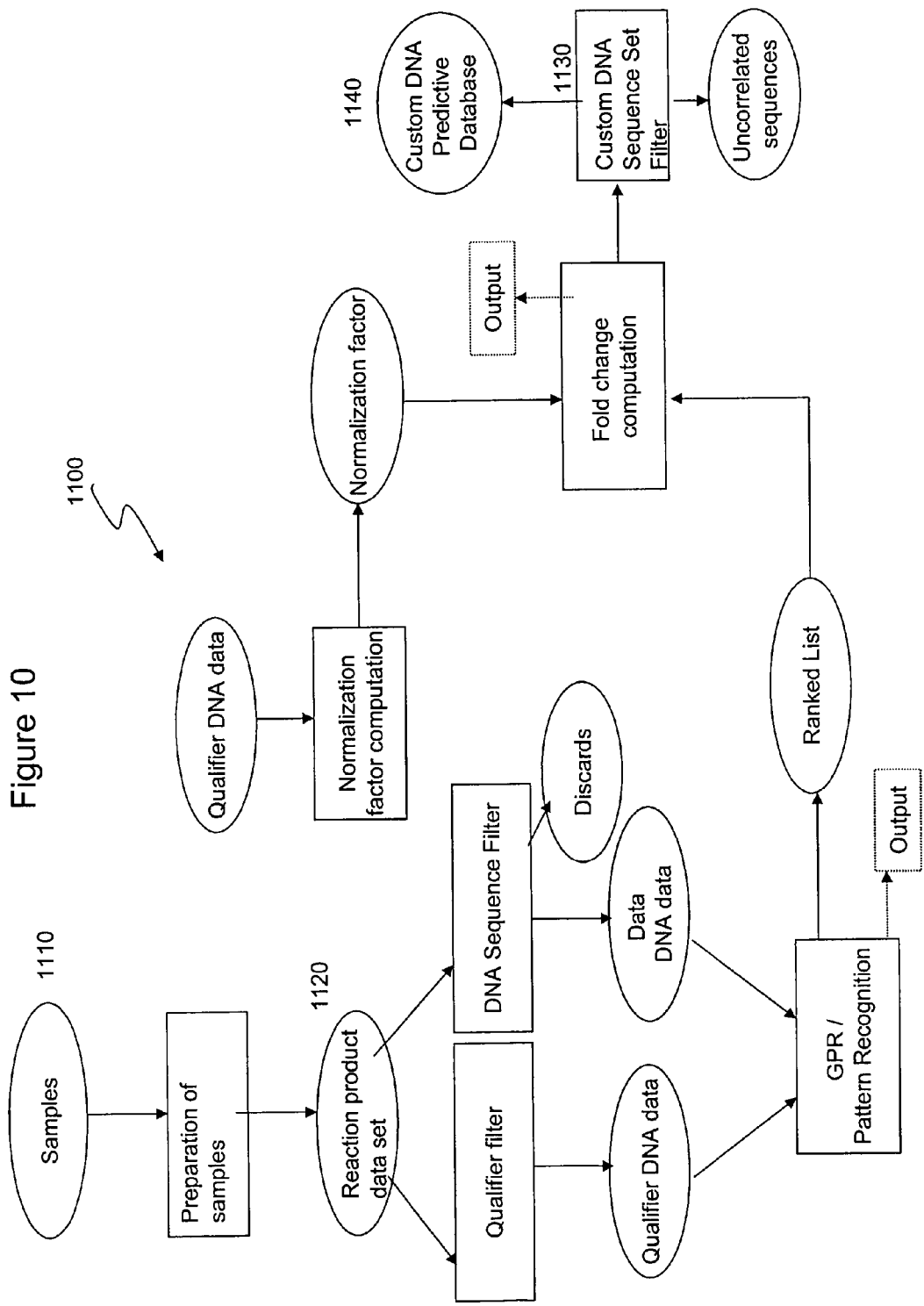
FIG. 10 depicts a block diagram illustrating a method for creating DNA sequence sets customized for evaluating and/or diagnosing a certain pathological condition.

In one aspect, as depicted in FIG. 10, the present invention can be used to create specific DNA sequence sets, or correlated sets, whose copy number variations may be indicators of particular conditions. These DNA sequence sets are included in a predictive database 1140 for that pathological condition. For example, a "lymphoma" DNA sequence set may include a set of DNA sequences whose variations are known to have a basis in lymphoma. The method 1100 would include furnishing samples 1110 including a sample derived from a known healthy subject and a sample derived from a subject known to be afflicted with a pathological condition of interest. A set of candidate DNA sequences is chosen as the target DNA sequences. The data associated with this set is included in the reaction product data set 1120. The method proceeds similarly to the method depicted in FIG. 1. However, in this method, a custom DNA sequence set filter 1130 identifies the candidate DNA sequences identified by the GPR step as having statistically significant variations in copy number as indicator DNA sequences for that pathological condition. It adds these DNA sequences into the custom DNA predictive database 1140. In this manner, a set of indicator DNA sequences associated with the pathological condition can be identified. The method 1100 is repeated with different DNA sequences included as target DNA sequences, and in this manner new DNA sequences are added to the predictive database 1140. This set of indicator DNA sequences 1140 can then be used as the set of target DNA sequences for the present invention in subsequent evaluative procedures for that pathological condition. For example, the genes listed in FIG. 9 with the highest GPR ranks can be included in a predictive database 1140 for B-cell lymphoma.

As mentioned above, multiple iterations of the method 1100 can be performed to determine DNA sequences to be included in the set 1140. In one aspect, in each iteration a different group of DNA sequences is included in the reaction product data set 1120. Criteria or rules are used to determine which genes to include as target DNA sequences in subsequent iterations. By way of example, if in one iteration of the method 1100 a particular gene is identified for inclusion in the custom DNA predictive database 1140, then in the subsequent iteration genes located in close chromosomal proximity, such as genes located in the same chromosomal region, as the included gene may be used as target DNA sequences. The process of choosing genes in subsequent iterations of the method 1100 for inclusion as target DNA sequences can be automated by using genes selected for inclusion in the predictive database 1140 as an input, and using criteria such as chromosomal proximity to automatically select other genes for inclusion as target DNA sequences in a subsequent iteration.

Various levels of customization can be achieved. For example, genetic profiles may be characteristic of not just certain pathological conditions, but also of certain stages of pathological conditions. Stages of cancerous conditions may be categorized based on the spread of cancer within the patient as mentioned above. By obtaining a sample known to be afflicted with a particular condition in a particular stage, using a method similar to that described above, DNA sequence sets catered to particular stages can be identified. Thus, in this aspect the invention is used to identify characteristic genetic profiles of particular stages of conditions, and also to evaluate a subject afflicted with a condition as being in a particular stage of that condition.

Another level of customization is defining DNA sequence sets specific to individual patients, or groups of related patients. For example, certain conditions may manifest themselves in unique ways with characteristic DNA sequence profiles for particular demographics.

In one aspect, the invention is used to create DNA sequence sets for cancers such as lymphoma, breast cancer, and lung cancer. As discussed above, the present invention is particularly well suited to collect and analyze samples derived from solid tumors of cancers. It can also be used with cancers that result in cystic tumors and/or tumors filled with liquid and/or pus. It can be used with broadly disseminated cancers such as leukemia. It can be used with cancers that have undergone metastasis.

In another aspect, the DNA sequences included in the custom DNA sequence set 1140 are entered in a predictive software database maintained for the pathological condition. The predictive software database can include identifiers for identifying the DNA sequences included in the custom DNA sequence set. The predictive software database can be used by a clinician to rapidly access DNA sequences that should be included in a custom DNA sequence set for a particular application. The predictive software database can provide a user interface and can be searchable.

Clinical Kits

The systems and methods described herein also provide a clinical kit for a pathological condition. The kit generally includes devices configured to implement the invention as described herein. A custom DNA sequence set includes DNA sequences for which the pathological condition serves as a basis of variation can be included in the kit. The set can be specifically chosen using methods described above. The kit can also include a computer and associated software to perform the GPR and fold change related steps mentioned above, such as an array pre-configured to handle these DNA sequences. The kit can also include a control sample and an experimental sample. If either or both of these sample types are to be provided by a clinician, then the kit includes means to gather the samples, such as a swab and/or biopsy tools. The kit can include DNA amplification/detection systems coupled to the array, such as those discussed above, for the purpose of collecting a reaction product data set. The kit can include a computer and associated software for automatically performing the processing steps described above, including determining a set of qualifier DNA sequences, normalizing with respect to them, providing a ranked list, and determining fold changes. The processing computer and software can be provided on, for example, a hand-held portable electronic device.

Experimental Design for GPR

In preferred embodiments, a plate of 96 DNA sequences or 384 DNA sequences is run for each biological replicate (usually 3 controls and 3 experimentals—although other preferred embodiments handle up to 5 controls and 5 experimentals). As described above, replicates may be technical replicates or biological replicates. It is possible to run fewer than 96 DNA sequences per biological replicate (e.g. 48 DNA sequences per subject, such that two samples can be fit onto one plate). The CT values for each replicate are then entered and analyzed by GPR. Thus for 6 animals (3 in each group) run against 96 DNA sequences, 6 runs may be run on the 7000/7700 (96-well format). Preferred embodiments include 4 animals in both comparison groups, and 5 may yield better results.

In one embodiment the plate comprises a one piece, injection-molded PCR plate in the industry standard 96-well format, providing handling convenience and compatibility with high throughput automated systems. Alternatives may be employed including, but not being limited to, polycarbonate plates, and plates of other sizes. The plates may be high profile or low profile, skirted or semi-skirted and the type of plate employed will depend upon the application at hand. In those practices, described in more detail below, where the GPR techniques described herein are applied to micro array, macro array or other array type datasets, the process may substitute arrays for plates.

Analyzing fewer than 96 DNA sequences per biological replicate is possible with GPR. To facilitate sample handling it is preferred to have a multiple of 24 DNA sequences per biological replicate (e.g. 24, 48, 96, 384). Results show that a minimum of 48 DNA sequences (with at least half of them remaining relatively unchanged between the two comparison groups) provides reliable data. The assumption is that most of the DNA sequences being analyzed will not change in a given experiment and therefore can be used as qualifiers. End users may empirically determine the minimum number of DNA sequence elements that provides them with reliable data.

ArrayGPR

As mentioned above, the invention is not limited to analyzing PCR-based data. For example, the GPR algorithm can also be used to analyze single or two-color microarray data. ArrayGPR, a program capable of analyzing up to 25,000 DNA sequences was created. Similar to 384GPR and 1536GPR, ArrayGPR calculates the microarray equivalent of $\Delta C_T$ values dynamically.

However, to handle microarray data in the GPR algorithm, the fluorescence intensity values generated from microarrays are first converted from linear values to logarithmic values (to resemble the logarithmic output of QPCR data). In addition, since higher values in microarray data denote higher amounts of DNA sequences while in QPCR, higher $C_T$ values denote lower amounts of DNA sequences, the values obtained from the log transform are multiplied by −1. The p-value behaves as before, however the user enters a value for the intensity cutoff (analogous to the Cycle Cutoff for QPCR/GPR). This value is also entered as a linear value, e.g. 150, which is converted by the program using a negative log transform. The transformed intensity cutoff is used exactly as the Cycle Cutoff was used to affect the DNA sequence and qualifier filters.

ArrayGPR will rank DNA sequences according to statistical significance, regardless of the magnitude of the change. Similar to the GPR programs for QPCR, in preferred embodiments the data is in the format of a column of values for each of the controls and the experimentals. This is the case whether the data for each sample was obtained in a single color or from a two color experiment.

Thus, ArrayGPR provides a useful alternative to the myriad approaches to "normalize" array data. In addition, since in any experimental manipulation, the copy number level of the vast majority of DNA sequences remains unchanged, ArrayGPR takes advantage of a huge number of qualifier DNA sequences to obtain a true global pattern of DNA profiling.

The GPR algorithm may also be applied to the analysis of "macroarrays" (e.g. Atlas™ blots) and to future protein arrays, and in reality to any array of DNA sequences analyzed across groups of (unpooled) control and experimental samples. In these cases, the data is linear and densitometric in nature. These data can be analyzed after the negative log transform function of ArrayGPR. Of course, the intensity cutoff values may have to be adjusted to account for differences in dynamic range among the various techniques, though the principle remains true. As for all GPR applications, samples should not be pooled and should be analyzed individually as controls and experimentals.

Further Applications of GPR

Those skilled in the art recognize that the methods disclosed herein are applicable to a wide variety of scientific problems. In general, the statistical methods described herein may be used for recognition of patterns and identification of differences in any datasets which include replicate images or data acquired before and after an event, alteration of conditions or other changes. The statistical concepts of the invention are based at least in part on statistical comparisons among the replicate images. This provides a statistical basis for damping out image variability and noise, thus revealing changes. Since this damping is performed computationally, it substantially reduces the bias and time-consuming need for human interpretation early in the analytic process. Changes that pass a specified cutoff can be flagged for inspection by an experienced technician or an automated system that detects changes beyond user-defined thresholds.

Datasets derived from any source or process may be analyzed and used in subsequent evaluations according to the methods. For example, certain applications extend to the use of photographic images to study changes in biological or other processes as shown, for example, by changes in a pixel dataset. In such embodiments, pixels in a photograph may be monitored over time to track changes in a property of interest (e.g., color, shading, image size) as depicted within each pixel. Control and experimental datasets for comparison may be formed with pixels derived over time (e.g., before and after an event). Individual pixel data (for example, grayscale value or intensity) may then be normalized to corresponding data in other pixels (i.e., the qualifier pixels) and then the control and experimental images/datasets can be compared as described previously. Statistical analyses similar to those described herein may be applied to assess changes in certain observed properties within pixels, and outputs analogous to those included in FIGS. 8a-b and 9 can be prepared to assist in the analysis of the changes occurring in the underlying processes.

In certain embodiments, at least one image containing a specific landmark location may be analyzed (analogous to a DNA sequence position in GPR) and used as input data. In certain embodiments, the image is analyzed at the level of at least one pixel or pixel block, each having a grayscale value that is used as input data (analogous to microarray data, this input is linear in nature and would preferably undergo a negative log transform prior to analysis). The number of shades of gray of an image may be increased or decreased as desired. Other pixels may also be selected and, in certain embodiments, more than one pixel may be collated and assigned as a referent pixel block. A grayscale value may be assigned to the reference pixel block. Subsequent images may be taken, for example after an event of interest, that also include the landmark location and other landmarks identified in the referent pixel or pixel block.

A pixel block may be any size, for example 10×10 pixels square (or much smaller (e.g., 2×4), or even much larger (e.g., 100×100)). The size of the block may be increased or decreased as desired. An arithmetic average or, preferably, a geometric mean may be calculated from grayscale values of the pixels within a block, and such value may be used as a data point for GPR analysis. An analogous value may be applied to each desired block within the image. The grayscale values (linear measures) are converted to logarithmic values by a negative log transformation.

In certain embodiments, images are taken of a subject both before and after a period of time, for example before and after an event of interest. Individual pixels or pixel blocks within each image are assigned gray scale values and analyzed to identify pixels or pixel blocks that have changed after the event of interest. The analysis, including its filtering and normalizing steps, is applied to the images as described above.

In certain embodiments, the methods may be applied to the analysis of medical images to assess the level of disease progression and the effects of disease treatment. The applications include the use of the algorithmic methods of the systems and methods to analyze changes in tissues, organs, and other physiological components as may be viewed by X-ray, CAT scan, photographs or any other medical imaging devices or modalities.

Replicate images obtained prior to treatment (e.g. surgery or chemotherapy for a tumor) may be compared to images obtained during or after treatment to highlight changes. Analysis may not only able to highlight changes in tumor size but collateral damage, extent of resection, new metastases, and other changes that might arise in the same image that may not be the subject of a technician's direct investigation. Additionally, CT and MRI scanners are able to collect data that is beyond the capacity of the human eye to perceive (i.e. far more shades of gray than can be perceived by the human eye), thus quantification of the grayscale values and analysis will allow the quantification of treatment effect (for example, through a GPR score) which is unbiased and beyond the limitations of a human observer.

For example, to assess whether a tumor has metastasized to the lungs, three Positron Emission Tomography (PET) images of a patient's thorax are taken in January. Three replicate images are then taken in April. The images are aligned using landmark pixels and single or blocks of grayscale pixels are subjected to the methods of the systems and methods, resulting in a ranked list based on the significance of change. The scores from the GPR step are then converted to a color scale and mapped back to the original image coordinates. The experienced technician may then use the color scaling to identify image features highlighted by high GPR score values. In this way, discrete image changes, such as the appearance of a small metastatic nodule, can be flagged and identified.

The methods are also useful for analyzing changes in concentration of certain biochemical components as a result of disease progression or treatment protocols. The techniques may also be applied to the analysis of biometric recognition studies (e.g., finger printing). Any data gathered with respect to changes in biochemical conditions (e.g., changes in plasma, tissue, or cellular concentration of biochemical or other components) may be analyzed using the methods described herein.

In still other embodiments, the techniques are applicable to the analysis of aerial and satellite photographs. For example, the methods described herein may be adapted to identify changes in planetary systems (e.g., to identify meteorites, comets, super novae, etc.), or even to study changes in surface properties of planets and other systems. In certain embodiments, replicate images are compared to highlight changes in a geographic space (e.g. erecting new buildings or tents, populating an area with troops and equipment, etc.). Gradual image changes, such as the assembly of a permanent structure, can be monitored by comparing replicate images over a wide time period. For example, three images may be taken in a week in January and compared to three images taken of the same subject space in a week in March. Image change over any period of time may be monitored. For example, rapid image changes, such as the deployment of troops to a new camp, may be monitored by comparing replicate images taken over a short period (for example images from three consecutive days with images from the next three consecutive days).

The same methodology is applicable to the rapid assessment of natural disasters. Other applicable changes may include changes in an ecosystem over time (e.g., by erosion, natural disaster, pollution), or even including military uses such as bomb damage assessments. For example, replicate images obtained prior to a bombing run can be compared to post-mission images to quickly highlight areas of damage (in a quantifiable manner with a GPR score). This type of analysis may also highlight areas of collateral damage.

In other embodiments, the methods are applied to the analysis of personal identification. Replicate past identification photos can be compared to current photos to assess areas of change, and areas that have not changed. For example, photographs of suspect faces taken in the past may be compared by the methods with more recent photographs to identify the subject. In certain embodiments, the lower the GPR score, the more likely the measured feature (e.g., a facial feature) has remained unchanged. This might be applied to identifying people before and after plastic/reconstructive surgery or in a more developed form for post-mortem identification with ante-mortem photographs.

In certain embodiments, GPR is employed to analyze disease progression in a subject, comprising furnishing an array of pixels taken from a medical image depicting properties of the subject; performing an analysis with the array to collect a property dataset; filtering the property dataset to identify a set of normalizer pixels; normalizing the property dataset using properties specific to the set of normalizer pixels; determining a ranking list using the normalized property dataset; and quantifying the changes in the pixels included in the ranked list.

In certain embodiments, an array is furnished analogously to the arrays described above, which may include providing a plurality of arrays having at least one control property. In certain embodiments, furnishing an array includes providing a plurality of arrays having at least one property of any type, including properties indicating the presence of a disease in a subject. Furnishing an array may also include forming a plurality of data points charting properties in control samples and experimental samples.

In certain embodiments, employing the methods of the systems and methods include measuring, for each pixel in an array, a parameter associated with a property representative of a threshold parameter (analogous to Cycle Cutoff for DNA sequence data). In certain embodiments filtering includes analyzing the property dataset to sort pixels into categories of qualifier pixels and data pixels. Filtering may also include removing from a property dataset pixels that depict a property that does not meet a specified threshold parameter.

In certain embodiments, normalizing a property dataset includes determining for a pixel differences in properties included in the respective pixel and in pixels in the identified set of qualifier pixels. The normalizing process compares each pixel or pixel block in a data set to determine differences in properties between each pixel, pixel block, etc., and the pixel or pixels identified in the set of qualifier pixels.

As noted, a ranking list of properties of interest may be developed by identifying a pattern of variance between properties shown in pixels associated with an experimental sample and corresponding properties shown in pixels associated with a control sample.

In certain embodiments, processing normalized data includes quantifying a pattern of variance between properties in a control group and properties in an experimental group and ranking properties as a function of the quantified pattern of variance. It may also include performing a T-test or other statistical analysis to identify a measure of similarity between a property in an experimental group and a property in a control group.

The methods also include tallying for a test pixel a score representative of a number of qualifier pixels depicting a statistically relevant variation in a property of interest.

The methods described herein can be operated on conventional data processing platforms such as an IBM PC-compatible computer running the Windows operating systems, or a SUN workstation running a Unix operating system. Alternatively, the data processing system can comprise a dedicated processing system that includes an embedded programmable data processing system that can include the processes described. For example, the data processing system can comprise a single board computer system that has been integrated into a system for performing microarray analysis. The single board computer (SBC) system can be any suitable SBC, including the SBCs sold by the Micro/Sys Company, which include microprocessors, data memory and program memory, as well as expandable bus configurations and an on-board operating system.

As discussed above, the GPR systems and methods can be realized as a software component operating on a conventional data processing system such as a Unix workstation. In that embodiment, the GPR system can be implemented as a C language computer program, or a computer program written in any high level language including C++, Fortran, Java or basic. Additionally, in an embodiment where microcontrollers or DSPs are employed, the GPR system can be realized as a computer program written in microcode or written in a high level language and compiled down to microcode that can be executed on the platform employed. The development of such systems is known to those of skill in the art, and such techniques are set forth in Digital Signal Processing Applications with the TMS320 Family, Volumes I, II, and III, Texas Instruments (1990). Additionally, general techniques for high level programming are known, and set forth in, for example, Stephen G. Kochan, Programming in C, Hayden Publishing (1983). It is noted that DSPs are particularly suited for implementing signal processing functions, including preprocessing functions such as image enhancement through adjustments in contrast, edge definition and brightness. Developing code for the DSP and microcontroller systems follows from principles well known in the art.

Those skilled in the art will know or be able to ascertain using no more than routine experimentation, many equivalents to the embodiments and practices described herein. Accordingly, it will be understood that the invention is not to be limited to the embodiments disclosed herein, but is to be understood from the following claims, which are to be interpreted as broadly as allowed under the law. All references identified herein are hereby incorporated by reference in their entireties.

We claim:

1. A method for determining the abundance of a genomic DNA sequence in an experimental sample relative to a control sample, comprising:
   (a) furnishing a control array and an experimental array, wherein the control and experimental arrays have a common set of primers for detecting genomic DNA sequences of interest;
   (b) performing a DNA detection process for the control sample using the control array to generate a control dataset;
   (c) performing a DNA detection process for the experimental sample using the experimental array to generate an experimental dataset;
   d) filtering each of the control and experimental datasets to identify a set of data DNA sequences, wherein the set of data DNA sequences consists of DNA sequences in either the control or experimental datasets with a value determined from the DNA detection process that is below a predetermined value;
   (e) filtering each of the control and experimental datasets to identify a set of qualifier DNA sequences, wherein the set of qualifier DNA sequences consists of DNA sequences which are present in both the control dataset and the experimental dataset with a value determined from the DNA detection process that is below a predetermined value;
   (f) normalizing each of the control and experimental datasets, comprising:
      (i) comparing the value of each data DNA sequence in the control dataset with the value of each qualifier DNA sequence in the control dataset to identify a control relative abundance value for each data DNA sequence-qualifier DNA sequence pair of the control dataset;
      (ii) comparing the value of each data DNA sequence in the experimental dataset with the value of each qualifier DNA sequence in the experimental dataset to identify an experimental relative abundance value for each data DNA sequence-qualifier DNA sequence pair of the experimental dataset;
   (g) comparing the control relative abundance value of a data DNA sequence-qualifier DNA sequence pair with the experimental relative abundance value of the corresponding data DNA sequence-qualifier DNA sequence pair, wherein a change in the relative abundance value indicates that the abundance of the data DNA sequence may be different in the experimental sample as compared that of the control sample; and
   (h) ranking the set of data DNA sequences based on the comparisons of relative abundance values in step (g).

2. The method of claim 1, wherein ranking the set of data DNA sequences comprises identifying a pattern of variation in the abundance of a data DNA sequence between the experimental sample and the control sample.

3. The method of claim 2, further comprising quantifying the pattern of variation and ranking the data DNA sequences as a function of the quantified pattern of variation.

4. The method of claim 1, further comprising:
   quantifying the relative abundance of a genomic DNA sequence in the experimental sample as compared to that of the control sample.

5. The method of claim 4, wherein said quantification determines the change of copy number of a genomic DNA sequence between the experimental sample and the control sample.

6. The method of claim 1, wherein the genomic DNA sequence is a gene.

7. The method of claim 1, wherein the genomic DNA sequence is a DNA fragment within a gene.

8. The method of claim 1, wherein the DNA detection process includes at least one of a DNA amplification process, a DNA signal detection process, or a DNA signal amplification process.

9. The method of claim 1, wherein the DNA detection process comprises performing a Real Time PCR (RT-PCR) analysis.

10. The method of claim 9, further comprising performing two or more replicate RT-PCR analyses for the control sample to generate the control dataset.

11. The method of claim 9, further comprising performing two or more replicate RT-PCR analyses for the experimental sample to generate the experimental dataset.

12. The method of claim 9, wherein filtering the control and experimental datasets comprises determining a RT-PCR cycle cut-off parameter.

13. The method of claim 12, wherein filtering the control and experimental datasets comprises discarding a DNA sequence having a RT-PCR cycle threshold above the cycle cut-off parameter.

14. The method of claim 12, wherein the relative abundance value for each data DNA sequence-qualifier DNA sequence pair is the difference in RT-PCR cycle thresholds between the data DNA sequence and qualifier DNA sequence.

15. The method of claim 1, wherein performing a DNA detection process comprises performing an isothermal DNA amplification process.

16. The method of claim 15, wherein the isothermal DNA amplification process is a rolling circle amplification.

17. The method of claim 15, wherein the isothermal DNA amplification process is a helicase-dependent amplification.

18. The method of claim 1, wherein step (g) further comprises:
   performing a statistical analysis comprising:
      for each of the data DNA sequence-qualifier DNA sequence pair, determining whether the difference between the control relative abundance value and the experimental relative abundance value is statistically significant.

19. The method of claim 18, wherein the statistical analysis is a T-test.

20. The method of claim 1, further comprising
   choosing one or more candidate DNA sequences to be a normalizer DNA sequence based on a numerical criterion associated with the reproducibility of detecting the candidate DNA sequence across the control sample and the experimental sample.

21. The method of claim 20, wherein determining the numerical criterion comprises:
   (i) determining sequences of numbers associated with relative quantities of the candidate DNA sequence with respect to other candidate DNA sequences across the control sample and the experimental sample,
   (ii) determining respective standard deviations of the sequences of numbers, and
   (iii) averaging the respective standard deviations.

22. The method of claim 21, further comprising:
   calculating a geometric mean of the numerical criteria of two or more normalizer DNA sequences, and using the geometric mean as a normalization factor.

23. A method of identifying a genomic DNA sequence whose copy number variation is correlated with a pathological condition, comprising:
  (1) obtaining a diseased sample from a subject having or potentially having the pathological condition;
  (2) comparing the copy number of a genomic DNA sequence in the diseased sample with the copy number of the corresponding genomic DNA sequence in a control sample, comprising:
    (a) furnishing a control array and a diseased array, wherein the control and diseased arrays have a common set of primers for detecting genomic DNA sequences of interest;
    (b) performing a DNA detection process for the control sample using the control array to generate a control dataset;
    (c) performing a DNA detection process for the diseased sample using the diseased array to generate a diseased dataset;
    (d) filtering each of the control and diseased datasets to identify a set of data DNA sequences, wherein the set of data DNA sequences consists of DNA sequences in either the control or diseased datasets with a value determined from the DNA detection process that is below a predetermined value;
    (e) filtering each of the control and diseased datasets to identify a set of qualifier DNA sequences, wherein the set of qualifier DNA sequences consists of DNA sequences which are present in both the control dataset and the diseased dataset with a value determined from the DNA detection process that is below a predetermined value;
    (f) normalizing each of the control and diseased datasets, comprising:
      (i) comparing the value of each data DNA sequence in the control dataset with the value of each qualifier DNA sequence in the control dataset to identify a control relative abundance value for each data DNA sequence-qualifier DNA sequence pair of the control dataset;
      (ii) comparing the value of each data DNA sequence in the diseased dataset with the value of each qualifier DNA sequence in the diseased dataset to identify a diseased relative abundance value for each data DNA sequence-qualifier DNA sequence pair of the diseased dataset;
    (g) comparing the control relative abundance value of a data DNA sequence-qualifier DNA sequence pair with the diseased relative abundance value of the corresponding data DNA sequence-qualifier DNA sequence pair, wherein a change in the relative abundance value indicates that the copy number of the data DNA sequence may be different in the diseased sample as compared to the copy number of the corresponding data DNA sequence in the control sample; and
    (h) ranking the set of data DNA sequences based on the comparisons of relative abundance values in step (g), wherein the rank identifies at least one genomic DNA sequence whose copy number variation is correlated with the pathological condition.

24. The method of claim 23, wherein ranking the set of data DNA sequences comprises identifying a pattern of variation in the copy number of a data DNA sequence between the diseased sample and the control sample.

25. The method of claim 24, further comprising quantifying the pattern of variation and ranking the data DNA sequences as a function of the quantified pattern of variation.

26. The method of claim 23, further comprising:
  quantifying the relative abundance of a genomic DNA sequence in the diseased sample as compared to that of the control sample.

27. The method of claim 26, wherein said quantification determines the change of copy number of a genomic DNA sequence between the diseased sample and the control sample.

28. The method of claim 23, wherein the genomic DNA sequence is a gene.

29. The method of claim 23, wherein the genomic DNA sequence is a DNA fragment within a gene.

30. The method of claim 23, wherein the DNA detection process includes at least one of a DNA amplification process, a DNA signal detection process, or a DNA signal amplification process.

31. The method of claim 23, wherein the DNA detection process comprises performing a Real Time PCR (RT-PCR) analysis.

32. The method of claim 31, further comprising performing two or more replicate RT-PCR analyses for the control sample to generate the control dataset.

33. The method of claim 31, further comprising performing two or more replicate RT-PCR analyses for the diseased sample to generate the diseased dataset.

34. The method of claim 31, wherein filtering the control and diseased datasets comprises determining a RT-PCR cycle cut-off parameter.

35. The method of claim 34, wherein filtering the control and diseased datasets comprises discarding a DNA sequence having a RT-PCR cycle threshold above the cycle cut-off parameter.

36. The method of claim 34, wherein the relative abundance value for each data DNA sequence-qualifier DNA sequence pair is the difference in RT-PCR cycle thresholds between the data DNA sequence and qualifier DNA sequence.

37. The method of claim 23, wherein step (g) further comprises:
  performing a statistical analysis comprising:
  performing a statistical analysis comprising:
  for each of the data DNA sequence-qualifier DNA sequence pair, determining whether the difference between the control relative abundance value and the diseased relative abundance value is statistically significant.

38. The method of claim 37, wherein the statistical analysis is a T-test.

39. The method of claim 23, further comprising
  choosing one or more candidate DNA sequences to be a normalizer DNA sequence based on a numerical criterion associated with the reproducibility of detecting the candidate DNA sequence across the control sample and the diseased sample.

40. The method of claim 39, wherein determining a numerical criterion comprises:
  (i) determining sequences of numbers associated with relative quantities of the candidate DNA sequence with respect to other candidate DNA sequences across the control sample and the diseased sample,
  (ii) determining respective standard deviations of the sequences of numbers, and
  (iii) averaging the respective standard deviations.

41. The method of claim 40, further comprising:
calculating a geometric mean of the numerical criteria of two or more normalizer DNA sequences, and using the geometric mean as a normalization factor.

42. The method of claim 23, wherein the control sample is from a subject who does not have or potentially have the pathological condition.

43. The method of claim 23, wherein the pathological condition is cancer.

44. The method of claim 23, wherein performing a DNA detection process comprises performing an isothermal DNA amplification process.

45. The method of claim 44, wherein the isothermal DNA amplification process is a rolling circle amplification.

46. The method of claim 44, wherein the isothermal DNA amplification process is a helicase-dependent amplification.EE

* * * * *

UNITED STATES PATENT AND TRADEMARK OFFICE
CERTIFICATE OF CORRECTION

PATENT NO. : 7,881,873 B2
APPLICATION NO. : 11/341699
DATED : February 1, 2011
INVENTOR(S) : Shreeram Akilesh et al.

It is certified that error appears in the above-identified patent and that said Letters Patent is hereby corrected as shown below:

Claim 37

Column 30, line 44, delete the 2nd "performing a statistical analysis comprising"

Claim 46

Column 32, line 8, delete "EE"

Signed and Sealed this
Thirtieth Day of August, 2011

David J. Kappos
*Director of the United States Patent and Trademark Office*